US009694556B2

(12) United States Patent
Turner et al.

(10) Patent No.: US 9,694,556 B2
(45) Date of Patent: *Jul. 4, 2017

(54) TUFTED FIBROUS WEB

(71) Applicant: The Procter & Gamble Company, Cincinnati, OH (US)

(72) Inventors: Robert Haines Turner, Cincinnati, OH (US); John Joseph Curro, Cincinnati, OH (US); Jody Lynn Hoying, Maineville, OH (US); Susan Nicole Lloyd, Erlanger, KY (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 364 days.

This patent is subject to a terminal disclaimer.

(21) Appl. No.: 14/185,960

(22) Filed: Feb. 21, 2014

(65) Prior Publication Data
US 2014/0170367 A1 Jun. 19, 2014

Related U.S. Application Data

(60) Continuation of application No. 13/409,145, filed on Mar. 1, 2012, now Pat. No. 8,697,218, which is a
(Continued)

(51) Int. Cl.
*B32B 5/26* (2006.01)
*B32B 7/02* (2006.01)
(Continued)

(52) U.S. Cl.
CPC ............ *B32B 5/12* (2013.01); *A44B 18/0011* (2013.01); *A61F 13/15707* (2013.01); *A61F 13/2068* (2013.01); *A61F 13/512* (2013.01); *B01D 39/1615* (2013.01); *B01D 39/1623* (2013.01); *B32B 3/28* (2013.01); *B32B 5/022* (2013.01);
(Continued)

(58) Field of Classification Search
CPC .. B32B 5/022; B32B 5/12; B32B 5/26; B32B 7/02; B32B 3/28; D04H 11/08
USPC .... 442/382, 381, 401; 428/88, 89, 170–172, 428/167
See application file for complete search history.

(56) References Cited

U.S. PATENT DOCUMENTS 2,068,456 A 1/1937 Hooper
2,275,425 A 3/1942 Grabec
(Continued)

FOREIGN PATENT DOCUMENTS

EP 0 509 012 B1 7/1995
FR 2 713 083 A1 6/1995
(Continued)

OTHER PUBLICATIONS

EPO Search Report, mailed May 9, 2011, 4 pages.

*Primary Examiner* — Jenna Johnson
(74) *Attorney, Agent, or Firm* — Dara M. Kendall; Andrew J. Hagerty

(57) ABSTRACT

Disclosed is a fibrous web having a first region and at least one discrete integral second region, the second region having at least one portion being a discontinuity exhibiting a linear orientation and defining a longitudinal axis, and at least another portion being a deformation having a plurality of tufted fibers integral with but extending from the first region.

22 Claims, 17 Drawing Sheets

Related U.S. Application Data continuation of application No. 12/881,535, filed on Sep. 14, 2010, now Pat. No. 8,153,225, which is a division of application No. 12/470,945, filed on May 22, 2009, now Pat. No. 7,829,173, which is a continuation of application No. 10/737,306, filed on Dec. 16, 2003, now Pat. No. 7,553,532, which is a continuation-in-part of application No. 10/435,996, filed on May 12, 2003, now abandoned, which is a continuation-in-part of application No. 10/324,661, filed on Dec. 20, 2002, now abandoned.

(51) Int. Cl.
| | |
|---|---|
| B32B 5/12 | (2006.01) |
| B32B 5/02 | (2006.01) |
| A44B 18/00 | (2006.01) |
| A61F 13/15 | (2006.01) |
| A61F 13/20 | (2006.01) |
| A61F 13/512 | (2006.01) |
| B01D 39/16 | (2006.01) |
| B32B 3/28 | (2006.01) |
| B32B 27/08 | (2006.01) |
| B32B 27/32 | (2006.01) |
| B32B 27/36 | (2006.01) |
| D04H 11/08 | (2006.01) |
| A47K 10/32 | (2006.01) |
| A61F 13/472 | (2006.01) |
| A61F 13/51 | (2006.01) |
| A61F 13/511 | (2006.01) |
| A61F 13/513 | (2006.01) |

(52) U.S. Cl.
CPC .......... *B32B 5/26* (2013.01); *B32B 7/02* (2013.01); *B32B 27/08* (2013.01); *B32B 27/32* (2013.01); *B32B 27/36* (2013.01); *D04H 11/08* (2013.01); *A47K 2010/3266* (2013.01); *A61F 13/472* (2013.01); *A61F 2013/51007* (2013.01); *A61F 2013/51178* (2013.01); *A61F 2013/51344* (2013.01); *A61F 2013/51355* (2013.01); *A61F 2013/51383* (2013.01); *B01D 2239/0604* (2013.01); *Y10T 428/2395* (2015.04); *Y10T 428/23914* (2015.04); *Y10T 428/23929* (2015.04); *Y10T 428/23936* (2015.04); *Y10T 428/23957* (2015.04); *Y10T 428/24289* (2015.01); *Y10T 428/24322* (2015.01); *Y10T 428/24339* (2015.01); *Y10T 428/24479* (2015.01); *Y10T 428/24612* (2015.01); *Y10T 428/24636* (2015.01); *Y10T 442/611* (2015.04); *Y10T 442/637* (2015.04); *Y10T 442/681* (2015.04)

(56) References Cited

U.S. PATENT DOCUMENTS

| | | | |
|---|---|---|---|
| 2,404,758 A | 7/1946 | Teague et al. | |
| 2,633,441 A | 3/1953 | Buttress | |
| 2,748,863 A | 6/1956 | Benton | |
| 2,924,863 A | 2/1960 | Chavannes | |
| 3,073,304 A | 1/1963 | Schaar | |
| 3,081,500 A | 3/1963 | Griswold et al. | |
| 3,081,512 A | 3/1963 | Griswold | |
| 3,137,893 A | 6/1964 | Gelpke | |
| 3,355,974 A | 12/1967 | Carmichael | |
| 3,511,740 A | 5/1970 | Sanders | |
| 3,542,634 A | 11/1970 | Such et al. | |
| 3,566,726 A | 3/1971 | Politis | |
| 3,579,763 A | 5/1971 | Sommer | |
| 3,681,182 A | 8/1972 | Kalwaites | |
| 3,681,183 A | 8/1972 | Kalwaites | |
| 3,684,284 A | 8/1972 | Tranfield | |
| 3,695,270 A | 10/1972 | Dostal | |
| 3,718,059 A | 2/1973 | Clayton | |
| 3,760,671 A | 9/1973 | Jenkins | |
| 3,881,987 A | 5/1975 | Benz | |
| 3,949,127 A | 4/1976 | Ostermeier et al. | |
| 3,965,906 A | 6/1976 | Karami | |
| 4,035,881 A | 7/1977 | Zocher | |
| 4,042,453 A | 8/1977 | Conway | |
| 4,135,021 A | 1/1979 | Patchell et al. | |
| 4,276,336 A | 6/1981 | Sabee | |
| 4,379,799 A | 4/1983 | Holmes | |
| 4,397,644 A | 8/1983 | Matthews et al. | |
| 4,465,726 A | 8/1984 | Holmes | |
| 4,469,734 A | 9/1984 | Minto et al. | |
| 4,588,630 A | 5/1986 | Shimalla | |
| 4,741,941 A | 5/1988 | Englebert et al. | |
| 4,758,297 A | 7/1988 | Calligarich | |
| 4,781,962 A | 11/1988 | Zamarripa et al. | |
| 4,798,604 A | 1/1989 | Carter | |
| 4,820,294 A | 4/1989 | Morris | |
| 4,840,829 A | 6/1989 | Suzuki et al. | |
| 4,859,519 A | 8/1989 | Cabe, Jr. et al. | |
| 4,886,632 A | 12/1989 | Van Iten et al. | |
| 4,935,087 A | 6/1990 | Gilman | |
| 4,953,270 A | 9/1990 | Gilpatrick | |
| 5,019,062 A | 5/1991 | Ryan et al. | |
| 5,026,587 A * | 6/1991 | Austin | B32B 5/26 15/209.1 |
| 5,062,418 A | 11/1991 | Dyer | |
| 5,144,730 A | 9/1992 | Dilo | |
| 5,165,979 A | 11/1992 | Watkins et al. | |
| 5,171,238 A | 12/1992 | Kajander | |
| 5,180,620 A | 1/1993 | Mende | |
| 5,188,625 A | 2/1993 | Van Iten et al. | |
| 5,223,319 A | 6/1993 | Cotton et al. | |
| 5,242,632 A | 9/1993 | Mende | |
| 5,382,245 A | 1/1995 | Thompson | |
| 5,383,870 A | 1/1995 | Takai et al. | |
| 5,387,209 A | 2/1995 | Yamamoto et al. | |
| 5,414,914 A | 5/1995 | Suzuki et al. | |
| 5,415,640 A | 5/1995 | Kirby et al. | |
| 5,429,854 A | 7/1995 | Currie et al. | |
| 5,437,653 A | 8/1995 | Gilman et al. | |
| 5,470,326 A | 11/1995 | Dabi et al. | |
| 5,508,080 A | 4/1996 | Sorimachi et al. | |
| 5,518,801 A | 5/1996 | Chappell et al. | |
| 5,533,991 A | 7/1996 | Kirby et al. | |
| 5,554,145 A | 9/1996 | Roe | |
| 5,560,794 A | 10/1996 | Currie et al. | |
| 5,567,501 A | 10/1996 | Srinivasan et al. | |
| D375,844 S | 11/1996 | Edwards et al. | |
| 5,573,719 A | 11/1996 | Fitting | |
| 5,575,874 A | 11/1996 | Griesbach, III et al. | |
| 5,580,418 A | 12/1996 | Alikhan | |
| 5,599,420 A | 2/1997 | Yeo et al. | |
| 5,624,427 A | 4/1997 | Bergman et al. | |
| 5,626,571 A | 5/1997 | Young et al. | |
| 5,628,097 A | 5/1997 | Benson et al. | |
| 5,648,142 A | 7/1997 | Phillips | |
| 5,656,119 A | 8/1997 | Srinivasan et al. | |
| 5,658,639 A | 8/1997 | Curro et al. | |
| 5,667,619 A | 9/1997 | Alikhan | |
| 5,667,625 A | 9/1997 | Alikhan | |
| 5,691,035 A | 11/1997 | Chappell et al. | |
| 5,700,255 A | 12/1997 | Curro | |
| 5,704,101 A | 1/1998 | Majors et al. | |
| 5,709,829 A | 1/1998 | Giacometti | |
| 5,714,107 A | 2/1998 | Levy et al. | |
| 5,723,087 A | 3/1998 | Chappell et al. | |
| 5,743,776 A | 4/1998 | Igaue | |
| 5,792,404 A | 8/1998 | Cree et al. | |
| 5,804,021 A | 9/1998 | Abuto et al. | |
| 5,814,389 A | 9/1998 | Giacometti | |
| 5,817,394 A | 10/1998 | Alikhan et al. | |
| 5,841,107 A | 11/1998 | Riva | |
| 5,858,504 A | 1/1999 | Fitting | |
| 5,879,494 A | 3/1999 | Hoff et al. | |

(56) References Cited

U.S. PATENT DOCUMENTS

| | | |
|---|---|---|
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,932,316 A * | 8/1999 | Cree .................. A61F 13/512 428/174 |
| 5,964,742 A | 10/1999 | McCormack et al. |
| 5,968,029 A | 10/1999 | Chappell |
| 5,986,167 A | 11/1999 | Arteman et al. |
| 5,990,377 A | 11/1999 | Chen et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,048,600 A * | 4/2000 | Hansson ............. A61F 13/512 428/132 |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,222,097 B1 | 4/2001 | McBride et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell |
| 6,479,130 B1 | 11/2002 | Takai et al. |
| D466,702 S | 12/2002 | Carlson et al. |
| 6,506,329 B1 | 1/2003 | Curro et al. |
| 6,537,936 B1 | 3/2003 | Busam et al. |
| 6,620,485 B1 | 9/2003 | Benson et al. |
| 6,626,961 B1 | 9/2003 | Everhart et al. |
| 6,632,504 B1 | 10/2003 | Gillespie et al. |
| D481,872 S | 11/2003 | Hennel et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,733,610 B2 | 5/2004 | Mizutani et al. |
| 6,736,916 B2 | 5/2004 | Steinke et al. |
| 6,794,626 B2 | 9/2004 | Copat et al. |
| 6,803,334 B2 | 10/2004 | Mizutani et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,863,960 B2 | 3/2005 | Curro et al. |
| 6,872,274 B2 | 3/2005 | Kauschke et al. |
| 6,884,494 B1 | 4/2005 | Curro et al. |
| 7,005,558 B1 | 2/2006 | Johansson et al. |
| 7,037,569 B2 | 5/2006 | Curro et al. |
| 7,172,801 B2 | 2/2007 | Hoying et al. |
| 7,270,861 B2 | 9/2007 | Broering et al. |
| 7,410,683 B2 | 8/2008 | Curro et al. |
| 7,507,459 B2 | 3/2009 | Turner et al. |
| 7,553,532 B2 | 6/2009 | Turner et al. |
| 7,579,062 B2 | 8/2009 | Cabell |
| 7,648,752 B2 | 1/2010 | Hoying et al. |
| 7,670,665 B2 | 3/2010 | Hoying et al. |
| 7,682,686 B2 | 3/2010 | Curro et al. |
| 7,718,243 B2 | 5/2010 | Curro et al. |
| 7,732,657 B2 | 6/2010 | Hammons et al. |
| 7,785,690 B2 | 8/2010 | Turner et al. |
| 2002/0035354 A1 | 3/2002 | Mirle et al. |
| 2002/0039867 A1 | 4/2002 | Curro et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2002/0192268 A1 | 12/2002 | Alwattari et al. |
| 2003/0021951 A1 | 1/2003 | Desai et al. |
| 2003/0085213 A1 | 5/2003 | Burckhardt et al. |
| 2003/0191442 A1 | 10/2003 | Bewick-Sonntag |
| 2003/0191443 A1 | 10/2003 | Taylor |
| 2004/0022993 A1 | 2/2004 | Wildeman |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1 | 12/2004 | Curro et al. |
| 2005/0064136 A1 | 3/2005 | Turner et al. |
| 2005/0096614 A1 | 5/2005 | Perez et al. |
| 2005/0123726 A1 | 6/2005 | Broering et al. |
| 2006/0019056 A1 | 1/2006 | Turner et al. |
| 2006/0087053 A1 | 4/2006 | O'Donnell et al. |
| 2006/0286343 A1 | 12/2006 | Curro et al. |
| 2008/0154226 A9 | 6/2008 | Hammons et al. |
| 2010/0036338 A1 | 2/2010 | Hammons et al. |
| 2010/0036346 A1 | 2/2010 | Hammons et al. |
| 2010/0036347 A1 | 2/2010 | Hammons et al. |
| 2010/0036352 A1 | 2/2010 | Hood et al. |
| 2010/0247844 A1 | 9/2010 | Curro et al. |
| 2010/0255258 A1 | 10/2010 | Curro et al. |

FOREIGN PATENT DOCUMENTS

| | | |
|---|---|---|
| FR | 2713083 A1 | 6/1995 |
| JP | 07-331574 A | 12/1995 |
| JP | 09-228229 A | 9/1997 |
| WO | WO 95/15138 | 6/1995 |
| WO | WO 01/45616 A1 | 6/2001 |
| WO | WO 01/76523 A2 | 10/2001 |
| WO | WO 02/100632 A1 | 12/2002 |
| WO | WO 2005/011936 A1 | 2/2005 |

* cited by examiner

TUFTED FIBROUS WEB

FIELD OF INVENTION

This invention relates to fibrous webs such as woven and nonwoven webs. In particular, this invention relates to fibrous webs treated by mechanical formation to have increased softness or bulk properties.

BACKGROUND OF THE INVENTION

Fibrous webs are well known in the art. For example, woven webs such as textile and knit fabrics are well known as material for clothing, upholstery, drapes, and the like. Also, nonwoven webs such as webs formed from polymer fibers are well known as materials useful for disposable products such as facing layers on absorbent articles such as diapers, for example.

In many applications it is desirable that fibrous webs have a bulky texture and/or softness. For example, textile wovens known as terry cloth have a bulky texture and softness and are often used for bath towels, wiping cloths, bibs, clothing, and upholstery fabric. Terry cloth is woven on specially made weaving machines, such as rapier weaving machines. Terry cloth is characterized by tufted loops of thread, and the tufts can be varied in number and density of loops. However, terry cloth is relatively expensive due to the relatively complex and expensive weaving machines necessary for its manufacture. The expense of terry cloth makes it commercially unfeasible for many applications, particularly for articles intended for limited use, such as disposable absorbent articles.

Attempts have been made to produce a nonwoven fabric having the appearance of terry cloth. For example, U.S. Pat. No. 4,465,726 and U.S. Pat. No. 4,379,799, both to Holmes et al., describe an apertured, ribbed terry cloth-like nonwoven fabric produced by fluid entangling of fibers on a special forming belt. Even if apertures could be avoided in the method disclosed in Holmes et al., it is well known that fluid entangling is a relatively expensive process for manufacture of nonwoven webs, particularly for webs intended for disposable article use. Furthermore, webs formed by fluid entangling typically have been subjected to forces of the fluid in all the regions of the web so that the entire web is subjected to the applied mechanical energy of the fluid forces.

Accordingly, there is a need for a low cost fibrous web having terry cloth-like properties.

Additionally, there is a need for a method for relatively inexpensively making a fibrous web having terry cloth-like properties.

Further, there is a need for a low cost method of making a soft, porous web of woven or nonwoven material.

SUMMARY OF THE INVENTION

A fibrous web having a first surface and a second surface is disclosed. The web comprises a first region and a plurality of discrete integral second regions, the second regions having at least one portion being a discontinuity exhibiting a linear orientation and defining a longitudinal axis, and at least another portion being a deformation comprising a plurality of tufted fibers integral with but extending from the first region.

DETAILED DESCRIPTION OF THE INVENTION

Figure 1:
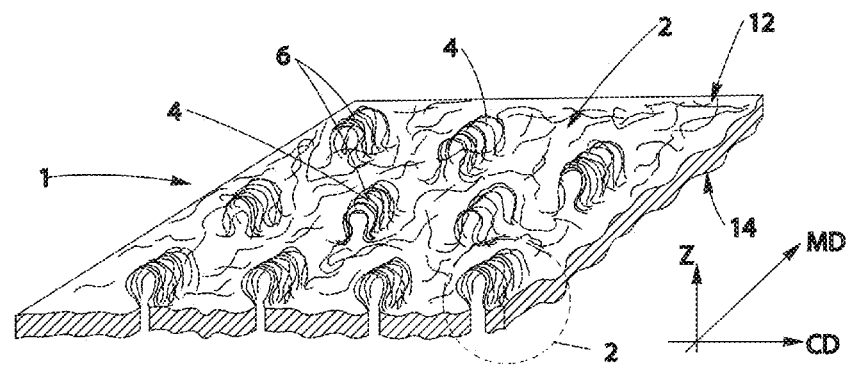
FIG. 1 is a perspective view of a web of the present invention.

FIG. 1 shows a web 1 of the present invention. Web 1 is formed from a generally planar, two dimensional nonwoven precursor web 20 (shown below with respect to the method of making) having a first surface 12 and a second surface 14, and having a machine direction (MD) and a cross machine direction (CD) as is commonly known in the art of nonwoven webs. First surface 12 corresponds to first "side" of web 1 and second surface 14 corresponds to the second "side" of web 1, the term "sides" being used in the common usage of generally two-dimensional webs, such as paper and films. Although the present invention can be practiced with woven webs, in a preferred embodiment precursor web 20 is a nonwoven web and is comprised of substantially randomly oriented fibers, that is, randomly oriented at least with respect to the MD and CD. By "substantially randomly oriented" is meant that, due to processing conditions, there may be a higher amount of fibers oriented in the MD than the CD, or vice-versa. For example, in spunbonding and meltblowing processes, continuous strands of fibers are deposited on a support moving in the MD. Despite attempts to make the orientation of the fibers of the spunbond or meltblown nonwoven web "random," usually a higher percentage of fibers are oriented in the MD as opposed to the CD.

Figure 2:
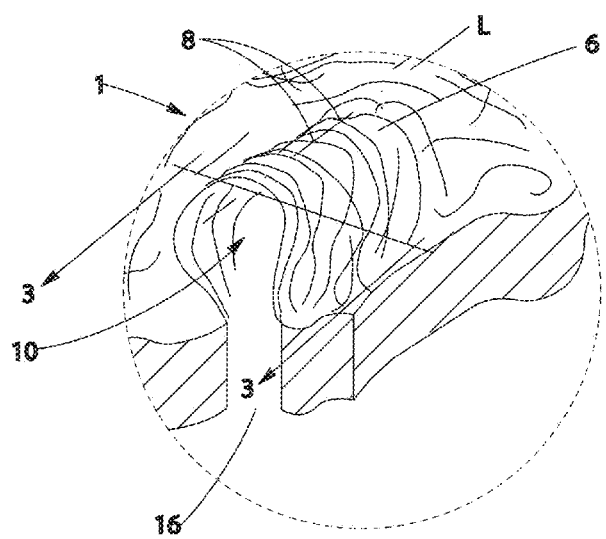
FIG. 2 is an enlarged view of a portion of the web shown in FIG. 1.
Figure 3:
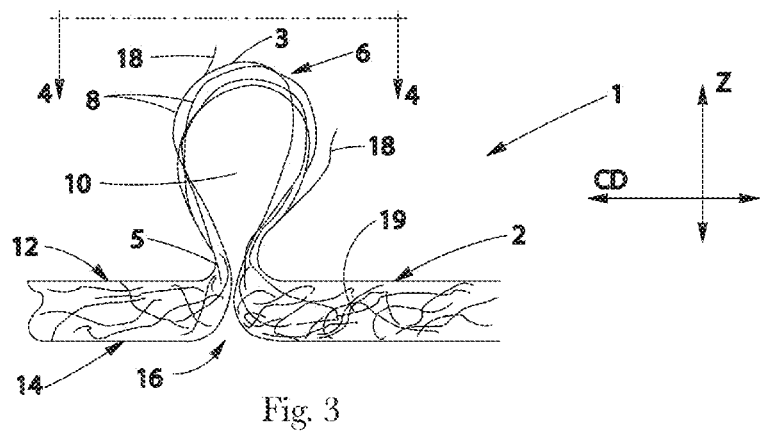
FIG. 3 is a cross-sectional view of section 3-3 of FIG. 2.

Nonwoven precursor webs 20 can be any known nonwoven webs comprising fibers having sufficient elongation properties to be formed into web 1 as described more fully below. As shown in FIG. 2, web 1 has a first region 2 defined on both sides of web 1 by the generally planar, two-dimensional configuration of the precursor web 20, and a plurality of discrete second regions 4 defined by spaced-apart deformations 6 and discontinuities 16 which result from integral extensions of the fibers of the precursor web 20. The structure of second regions 4 is differentiated depending on which side of web 1 is considered. For the embodiment of web 1 shown in FIG. 1, on the side of web 1 associated with first surface 12 of web 1, second region 4 comprises deformations 6, each deformation 6 comprising a plurality of tufted, looped, aligned fibers 8 extending outwardly from first surface 12. Deformations 6 can be described as "tufts" of fibers, and each deformation 6 has a base 5 proximal to the first surface 12, and a distal portion 3 at a maximum distance from first surface 12, as shown in FIG. 3. On the side of web 1 associated with second surface 14, second region 4 comprises discontinuities 16 which are defined by fiber orientation discontinuities on second surface 14 of web 1. As shown below, in other embodiments of web 1, the deformations 6 may be described as tufts, or tufted, but may not comprise looped or aligned fibers.

As used herein, the term "nonwoven web" refers to a web having a structure of individual fibers or threads which are interlaid, but not in a repeating pattern as in a woven or knitted fabric, which do not have randomly oriented fibers. Nonwoven webs or fabrics have been formed from many processes, such as, for example, meltblowing processes, spunbonding processes, hydroentangling processes, spunlacing processes, airlaying, and bonded carded web processes. The basis weight of nonwoven fabrics is usually expressed in grams per square meter (gsm) and the fiber diameters are usually expressed in microns. Fiber size can also be expressed in denier. The basis weight of precursor web 20 can range from 10 gsm to 500 gsm, depending on the ultimate use of the web 1. For use as a hand towel, for example, a basis weight of precursor web 20 of between 25 gsm and 100 gsm may be appropriate. For use as a bath towel a basis weight of between 125 gsm and 250 gsm may be appropriate. For use as a ground cover, such as a cow carpet, a basis weight of between 350 gsm and 500 gsm may be appropriate. The constituent fibers of nonwoven precursor web 20 can be comprised of polymers such as polyethylene, polypropylene, polyester, and blends thereof. The fibers can comprise cellulose, rayon, cotton, or other natural materials or blends of polymers and natural materials. The fibers can also comprise a super absorbent material such as polyacrylate or any combination of suitable materials. The fibers can be monocomponent, bicomponent and/or biconstituent, round, non-round fibers (e.g., shaped fibers or capillary channel fibers), and can have major cross-sectional dimensions (e.g., diameter for round fibers) ranging from 0.1-500 microns. For example, one type of fibers suitable for the nonwoven web includes nanofibers. Nanofibers are described as fibers having a mean diameter of less than 1 micron. Nanofibers can comprise all of the fibers in a nonwoven web or a portion of the fibers in a nonwoven web. The constituent fibers of the precursor web may also be a mixture of different fiber types, differing in such features as chemistry, components, diameter, shape, and the like.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement, each as is known in the art of multicomponent, including bicomponent, fibers. Bicomponent fibers can be splittable fibers, such fibers being capable of being split lengthwise before or during processing into multiple fibers each having a smaller cross-sectional dimension than the original bicomponent fiber. Splittable fibers have been shown to produce softer nonwoven webs due to their reduced cross-sectional dimensions. Representative splittable fibers useful in the present invention include type T-502 and T-512 16 segment PET/nylon 6 2.5 denier fibers;

and type T-522 16 segment PET/PP splittable fibers, all available from Fiber Innovation Technology, Johnson City, Tenn.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

As used herein, the term "integral" as in "integral extension" when used of the second regions 4 refers to fibers of the second regions 4 having originated from the fibers of the precursor web 20. Therefore, the looped fibers 8 of deformations 6, for example, can be plastically deformed and extended fibers of the precursor web 20, and are, therefore, integral with first regions 2 of web 1. As used herein, "integral" is to be distinguished from fibers introduced to or added to a separate precursor web for the purpose of making tufts, as is commonly done in conventional carpet making, for example. It can be appreciated that a suitable nonwoven web 20 should comprise fibers capable of experiencing sufficient plastic deformation and tensile elongation, or are capable of sufficient fiber mobility such that looped fibers 8 are formed. However, it is recognized that a certain percentage of fibers urged out of the plane of the first surface 12 of the precursor web 20 will not form a loop, but instead will break and form loose ends. Such fibers are referred to herein as "loose" or "broken" fibers 18 as shown in FIG. 3. Loose fiber ends 18 can also be the result of forming deformations 6 from nonwoven webs consisting of or containing cut staple fibers. Loose fiber ends 18 are not necessarily undesirable for the present invention, but it is believed that web 1 can retain its bulky and soft character more readily when deformation 6 comprises primarily looped fibers 8. In a preferred embodiment, at least about 50%, more preferably at least 70%, and most preferably at least 90% of fibers urged in the Z-direction are looped fibers 8.

A representative deformation 6 for the embodiment of web 1 shown in FIG. 1 is shown in a further enlarged view in FIG. 2. As shown, deformation 6 comprises a plurality of looped fibers 8 that are substantially aligned such that deformation 6 has a distinct longitudinal orientation and a longitudinal axis L. Deformations 6 also have a transverse axis T generally orthogonal to longitudinal axis L in the MD-CD plane. In the embodiment shown in FIGS. 1 and 2, longitudinal axis L is parallel to the MD. In one embodiment, all the spaced apart deformations 6 have generally parallel longitudinal axes L. The number of deformations 6 per unit area of web 1, i.e., the area density of deformations 6, can be varied from 1 deformation 6 per square centimeter to as high as 100 deformations 6 per square centimeter.

There can be at least 10, or at least 20 deformations 6 per square centimeter, depending on the end use. In general, the area density need not be uniform across the entire area of web 1, but deformations 6 can be only in certain regions of web 1, such as in regions having predetermined shapes, such as lines, stripes, bands, circles, and the like.

Figure 4:
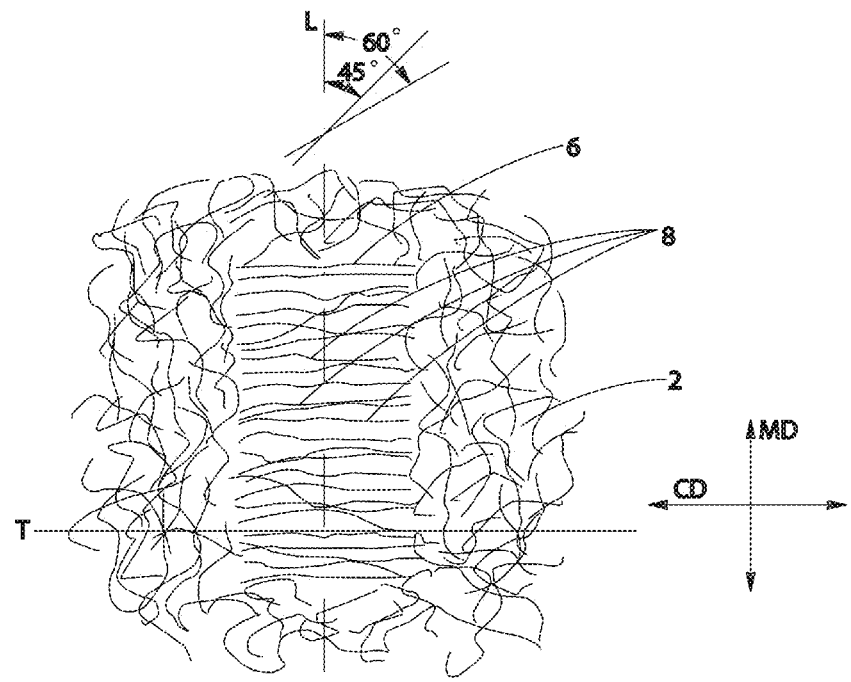
FIG. 4 is a plan view of a portion of the web as indicated by 4-4 in FIG. 3.

As shown in FIG. 2, and more clearly in FIGS. 3 and 4, one characteristic of the fibers 8 of deformations 6 in one embodiment of web 1 is the predominant directional alignment of the looped fibers 8. As shown in FIGS. 3 and 4, the looped fibers 8 have a substantially uniform alignment with respect to transverse axis T when viewed in plan view, such as in FIG. 4. By "looped" fibers 8 is meant that fibers 8 begin and end in web 1. By "aligned" with respect to looped fibers 8 of deformations 6 is meant that looped fibers 8 are all generally oriented such that, if viewed in plan view as in FIG. 4, each of the looped fibers 8 has a significant vector component parallel to the transverse axis T, and preferably a major vector component parallel to the transverse axis T. As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. In a preferred embodiment, at least 50%, more preferably at least 70%, and more preferably at least 90% of fibers 8 of deformation 6 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L.

The orientation of looped fibers 8 in the deformations 6 of second region 4 is to be contrasted with the fiber composition and orientation of the first region 2, which, for nonwoven precursor webs 20 is best described as having a substantially randomly-oriented fiber alignment. In a woven web embodiment, the orientation of the looped fibers 8 in deformations 6 could be the same as described above, but the fibers of second region 2 would have the orientation associated with the particular weaving process used to make the web, e.g., a square weave pattern.

In the embodiment shown in FIG. 1 the longitudinal axes L of deformations 6 are generally aligned in the MD. Deformations 6 and, therefore, longitudinal axes L, can, in principle, be aligned in any orientation with respect to the MD or CD. Therefore, in general, it can be said that for each deformation 6, the looped aligned fibers 8 are aligned generally orthogonal to the longitudinal axis L such that they have a significant vector component parallel to transverse axis T, and more preferably a major vector component parallel to transverse axis T.

Figure 5:
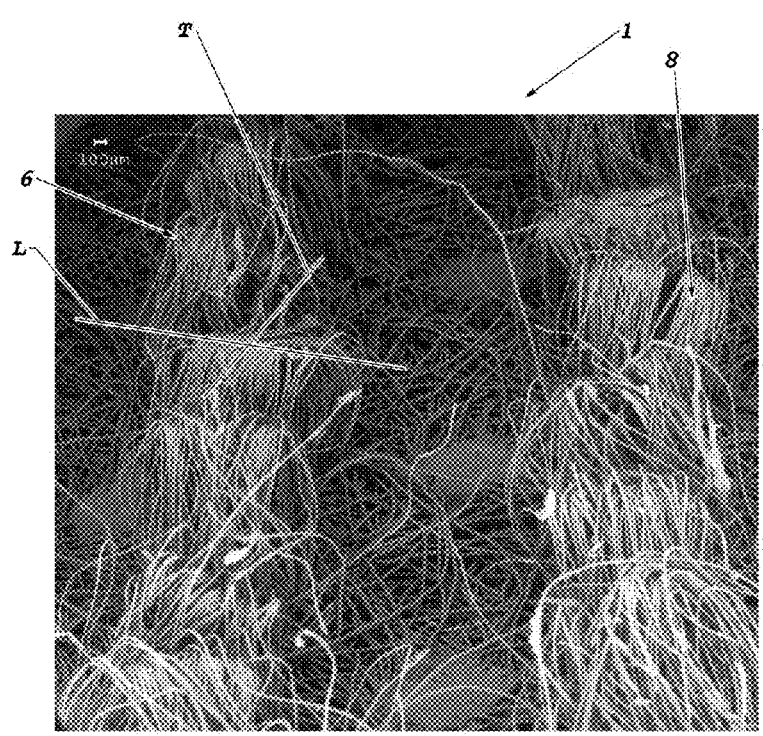
FIG. 5 is a photomicrograph of a portion of a web of the present invention.

FIG. 5 is a scanning electron microscope (SEM) photo of a web 1 similar to that described with respect to FIG. 1. The web 1 of FIG. 5 is a 70 gsm spunbond nonwoven web comprising polyethylene/polypropylene (sheath/core) bicomponent fibers. The perspective of FIG. 5 is essentially a side view of the first surface 2 and deformations 6 of web 1. By "side view" is meant that the photo of FIG. 5 is taken generally in the CD direction as indicated in FIGS. 1-4, such that the MD and longitudinal axes L of each deformation 6 are oriented across (e.g., generally horizontally) in FIG. 5.

As shown in FIG. 5, deformations 6 comprise looped aligned fibers 8 are aligned generally orthogonal to the longitudinal axis L and have at least a significant vector component parallel to transverse axis T.

Figure 6:
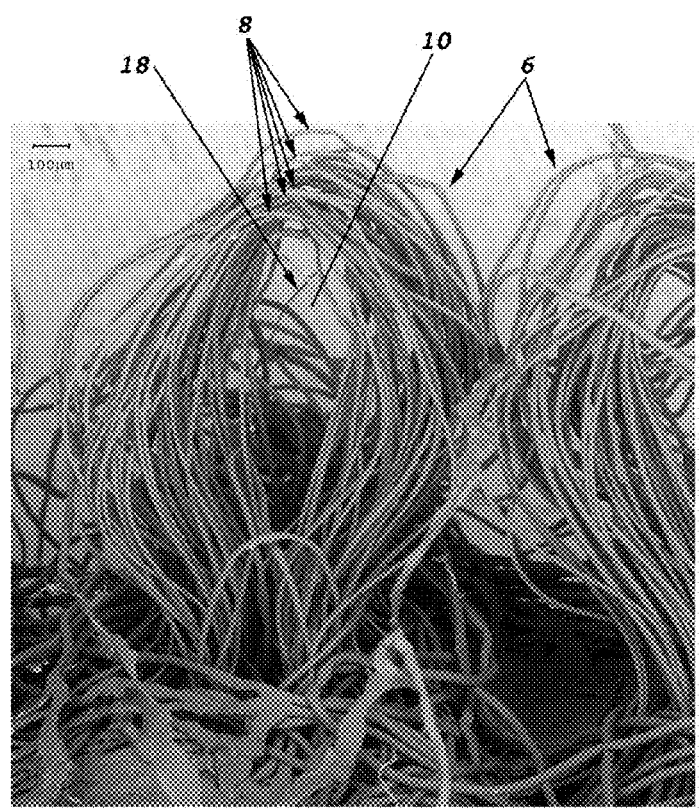
FIG. 6 is a photomicrograph of a portion of the web of FIG. 5.

In some embodiments, due to the preferred method of forming deformations 6, as described below, another characteristic of deformations 6 is their generally open structure characterized by open void area 10 defined interiorly of deformations 6, as shown in FIG. 3. The void area 10 may have a shape that is wider or larger at the distal 3 end of deformation 6 and narrower at the base 5 of the deformation 6. This shape is opposite to the shape of the tooth which is used to form the deformation 6. By "void area" is not meant completely free of any fibers, but is meant as a general description of its general appearance. Therefore, it may be that in some deformations 6 a loose fiber 8 or a plurality of loose fibers 8 may be present in the void area 10. By "open" void area is meant that the two longitudinal ends of deformation 6 are generally open and free of fibers, such that deformation 6 forms something like a "tunnel" structure, as shown in FIG. 3. For example, FIG. 6 is a close-up SEM view of one deformation 6 of the web 1 shown in FIG. 5. As shown, in addition to the looped aligned fibers 8 there is a distinct open void area 10 defined by a plurality of looped aligned fibers 8. Very few broken fibers 18 are visible. As can be seen, the base 5 of the deformation 6 may be closed (as in the fibers forming the deformation 6 are close enough together to touch) or may remain open. Generally, any opening at the base 6 is narrow.

Additionally, as a consequence of a preferred method of making web 1, the second regions 4 associated with second surface 14 are discontinuities 16 characterized by a generally linear indentation defined by formerly random fibers of the second surface 14 having been urged directionally (i.e., the "Z-direction" as is commonly understood in the nonwoven art to indicate an "out-of-plane" direction generally orthogonal to the MD-CD plane as shown in FIGS. 1 and 3) into deformation 6 by the teeth of the forming structure, described in detail below. The abrupt change of orientation exhibited by the previously randomly-oriented fibers of precursor web 20 defines the discontinuity 16, which exhibits a linearity such that it can be described as having a longitudinal axis generally parallel to longitudinal axis L of the deformation 6. Due to the nature of many nonwoven webs useful as precursor webs 20, discontinuity 16 may not be as distinctly noticeable as deformations 6. For this reason, the discontinuities 16 on the second side of web 1 can go unnoticed and may be generally undetected unless web 1 is closely inspected. Thus in some embodiments, web 1 has the look and feel of terry cloth on a first side, and a relatively smooth, soft look and feel on a second side. In other embodiments, discontinuities 16 can appear as apertures, and may be apertures through web 1 via the ends of the tunnel-like looped deformations 6.

Further, as a consequence of a preferred method of making web 1, whether or not the second regions 4 have looped aligned fibers 8, each exhibits a pronounced linearity at or near the first and second surfaces 12, and 14, respectively, of web 1. As disclosed more fully below with respect to the method of making, one can appreciate that, due to the geometry of teeth 110 of roll 104, the second regions 4 of precursor web 20 each have a linear orientation associated therewith. This linear orientation is an inevitable consequence of the method of making web 1 as described herein. One way of understanding this linear orientation is to consider the linear orientation of discontinuities 16 on the second surface 14 of web 1. Likewise, if deformation 6 were removed from web 1 at first surface 12, the second region 4 would appear as a linear discontinuity on the first surface 12 of web 1, e.g., as if a linear slit or cut had been made in precursor web 20 at the location of deformation 6. This linear web discontinuity corresponds directionally to longitudinal axis L.

From the description of web 1, it can be seen that the looped fibers 8 of deformation 6 can originate and extend from either the first surface 12 or the second surface 14 of web 1. Of course the fibers 8 of deformation 6 can also extend from the interior 19 of web 1. The fibers 8 of deformations 6 extend due to having been urged out of the generally two-dimensional plane of precursor web 20 (i.e., urged in the "Z-direction" as shown in FIG. 3). In general, the fibers 8 or 18 of the second regions 4 comprise fibers that are integral with and extend from the fibers of the fibrous web first regions 2.

Therefore, from the above description, it is understood that in one embodiment web 1 can be described as being a fibrous web 1 having a first surface 12 and a second surface 14, the fibrous web 1 comprising a first region 2 and a plurality of discrete integral second regions 4, the second regions 4 having at least one portion being a discontinuity 16 exhibiting a linear orientation and defining a longitudinal axis L and at least another portion being a deformation 6 comprising a plurality of tufted fibers integral with but extending from the first region 2.

The extension of looped fibers 8 can be accompanied by a general reduction in fiber cross sectional dimension (e.g., diameter for round fibers) due to plastic deformation of the fibers and the effects of Poisson's ratio. Therefore, the fibers 8 of deformation 6 can have an average fiber diameter less than the average fiber diameter of the fibers of precursor web 20 as well as the fibers of first regions 2. It is believed that this reduction in fiber diameter contributes to the perceived softness of the web 1, a softness that can be comparable to cotton terry cloth, depending on the material properties of the precursor web 20. It has been found that the reduction in fiber cross-sectional dimension is greatest intermediate the base 5 and the distal portion 3. This is believed to be due to the method of making, as disclosed more fully below. Briefly, it is believed that portions of fibers at the base 5 and distal portion 3 of deformations 6 are adjacent the tip of teeth 110 of roll 104, described more fully below, and are frictionally locked and immobile during processing. Thus, the intermediate portions of deformations 6 are more free to stretch, or elongate, and accordingly, are more free to experience a corresponding fiber cross sectional dimension reduction.

Figure 7:
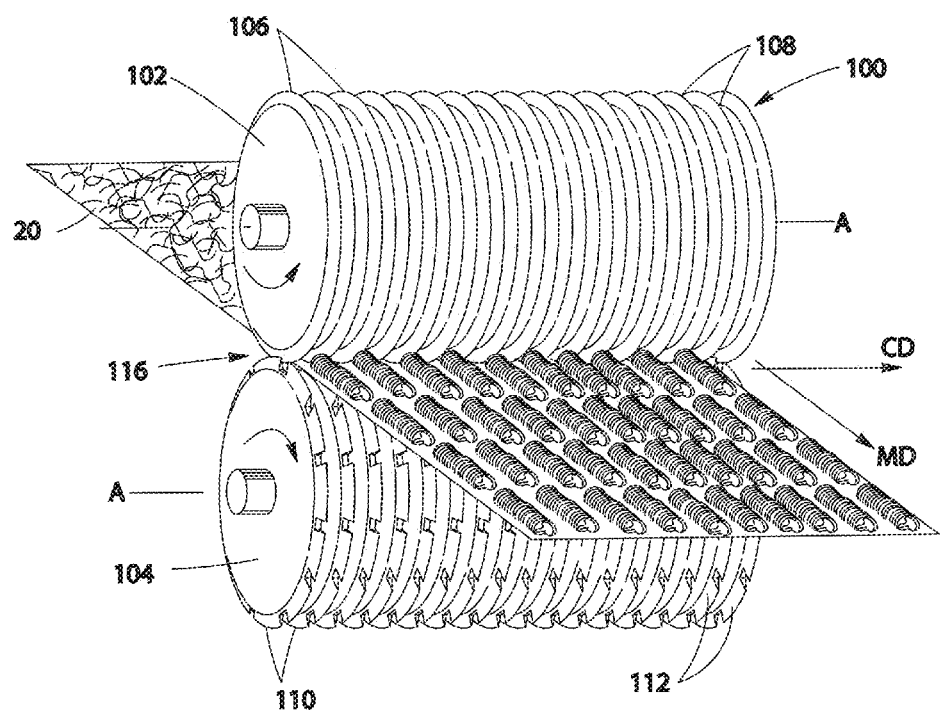
FIG. 7 is a perspective view of an apparatus for forming the web of the present invention.

Referring to FIG. 7 there is shown in an apparatus and method for making web 1 of the present invention. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 8, discussed below. Both or either of rolls 102 and 104 can be heated by means known in the art such as by using hot oil filled rollers or electrically-heated rollers.

In FIG. 7, the apparatus 100 is shown in a preferred configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with deformations protruding from both sides of the web 1.

The method of making a web 1 of the present invention in a commercially viable continuous process is depicted in FIG. 7. Web 1 is made by mechanically deforming a precursor web 20 that can be described as generally planar and two-dimensional. By "planar" and "two dimensional" is meant simply that the web is flat relative to the finished web 1 that has distinct, out-of-plane, Z-direction three-dimensionality imparted due to the formation of second regions 4. "Planar" and "two-dimensional" are not meant to imply any particular flatness, smoothness or dimensionality.

The process described is similar in many respects to a process as described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus of the present invention and the apparatus disclosed in the above-identified '801 patent. These differences account for the novel features of the web of the present invention. As described below, the teeth 110 of roll 104 have a specific geometry associated with the leading and trailing edges that permit the teeth, e.g., teeth 110, to essentially "punch" through the precursor web 20 as opposed to, in essence, emboss the web. The difference in the apparatus 100 of the present invention results in a fundamentally different web. For example, a web 1 of the present invention can have distinctive "tunnel-like" tufted deformations 6 of looped, aligned fibers 8, unlike the "tent-like" rib-like elements of prior art SELF webs which each have continuous side walls associated therewith, i.e., a continuous "transition zone." It is believed that the distinctive "tunnel-like" tufted deformations 6 of the web 1 of the present invention contribute to the superior fluid handling properties of web 1 by permitting fluid entry into and through web 1 via void regions 10 of deformations 6.

Precursor web 20 is provided either directly from a web making process or indirectly from a supply roll (neither shown) and moved in the machine direction to the nip 116 of counter-rotating intermeshing rolls 102 and 104. Precursor web can be a nonwoven web comprising any of known fiber types, including bicomponent fibers, capillary channel fibers, microfibers or splittable fibers. Precursor web 20 can be preheated by means known in the art, such as by heating over oil-heated rollers. Furthermore, precursor web can be a nonwoven web made by known processes, such as melt-blown, spunbond, and carded. As precursor web 20 goes through the nip 116 the teeth 110 of roll 104 enter grooves 108 of roll 102 and simultaneously urge fibers out of the plane of plane of precursor web 20 to form second regions 2, including deformations 6 and discontinuities 16. In effect, teeth 110 "push" or "punch" through precursor web 20. As the tip of teeth 110 push through precursor web 20 the portions of fibers that are oriented predominantly in the CD and across teeth 110 are urged by the teeth 110 out of the plane of precursor web 20 and are stretched, pulled, and/or plastically deformed in the Z-direction, resulting information of second region 4, including the looped fibers 8 of deformations 6 of web 1. Fibers that are predominantly oriented generally parallel to the longitudinal axis L, i.e., in the machine direction of precursor web 20 as shown in FIG. 1, are simply spread apart by teeth 110 and remain substantially in the first region 2 of web 1. Although, as discussed more fully below, it has been found that the rate of formation of deformations 6 affects fiber orientation, in general, and at least at low rates of formation, it can be understood why the looped fibers 8 can exhibit the unique fiber orientation which is a high percentage of fibers having a significant or major vector component parallel to the transverse axis T of deformation 6, as discussed above with respect to FIGS. 3 and 4. In general, at least some of the fibers of deformation 6 are looped, aligned fibers 8 which can be described as having a significant or major vector component parallel to a Z-oriented plane orthogonal to transverse axis T.

The number, spacing, and size of deformations 6 can be varied by changing the number, spacing, and size of teeth 110 and making corresponding dimensional changes as necessary to roll 104 and/or roll 102. This variation, together with the variation possible in precursor webs 20 and line speeds, permits many varied webs 1 to be made for many purposes. For example, web 1 made from a high basis weight textile fabric having MD and CD woven extensible threads could be made into a soft, porous ground covering, such as a cow carpet useful for reducing udder and teat problems in cows. A web 1 made from a relatively low basis weight nonwoven web of extensible spunbond polymer fibers could be used as a terry cloth-like fabric for semi-durable or durable clothing. As described more fully below, web 1 can also be used in disposable absorbent articles.

Figure 8:
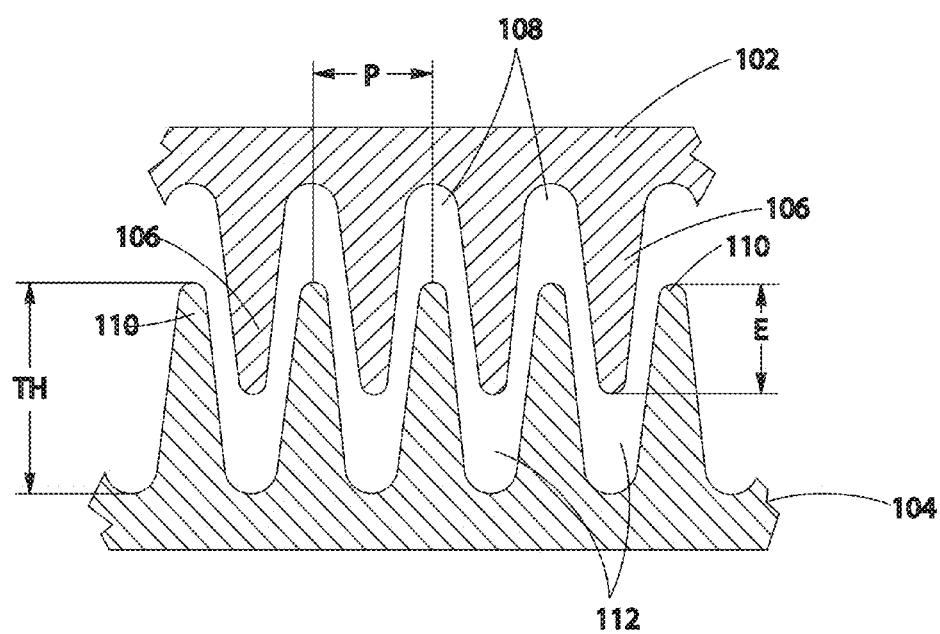
FIG. 8 is a cross-sectional depiction of a portion of the apparatus shown in FIG. 7.

FIG. 8 shows in cross section a portion of the intermeshing rolls 102 and 104 including ridges 106 and teeth 110. As shown teeth 110 have a tooth height TH (note that TH can also be applied to ridge 106 height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor web 20 and the desired characteristics of web 1. For example, in general, to obtain looped fibers in deformation 6, the greater the level of engagement E, the greater the necessary fiber mobility and/or elongation characteristics the fibers of precursor web 20 must possess. Also, the greater the density of second regions 4 desired (second regions 4 per unit area of web 1), the smaller the pitch should be, and the smaller the tooth length TL and tooth distance TD should be, as described below.

Figure 9:
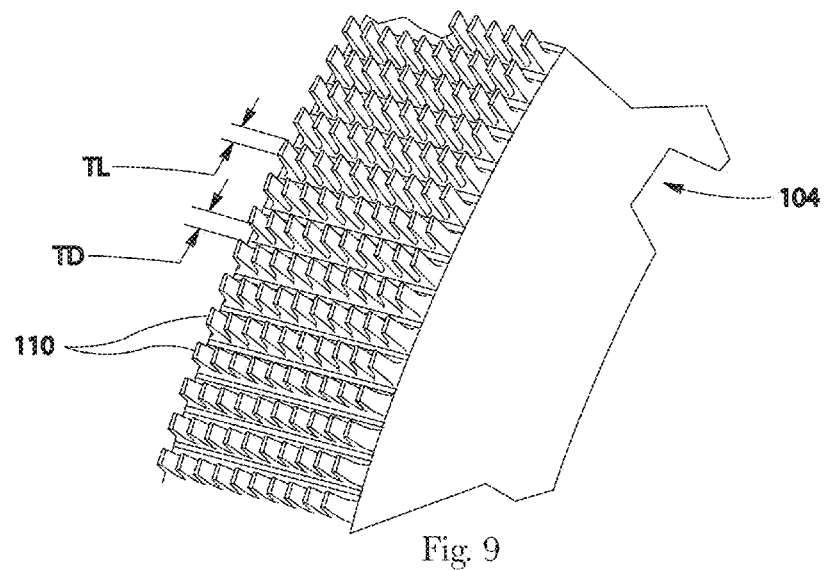
FIG. 9 is a perspective view of a portion of the apparatus for forming one embodiment the web of the present invention.
Figure 10:
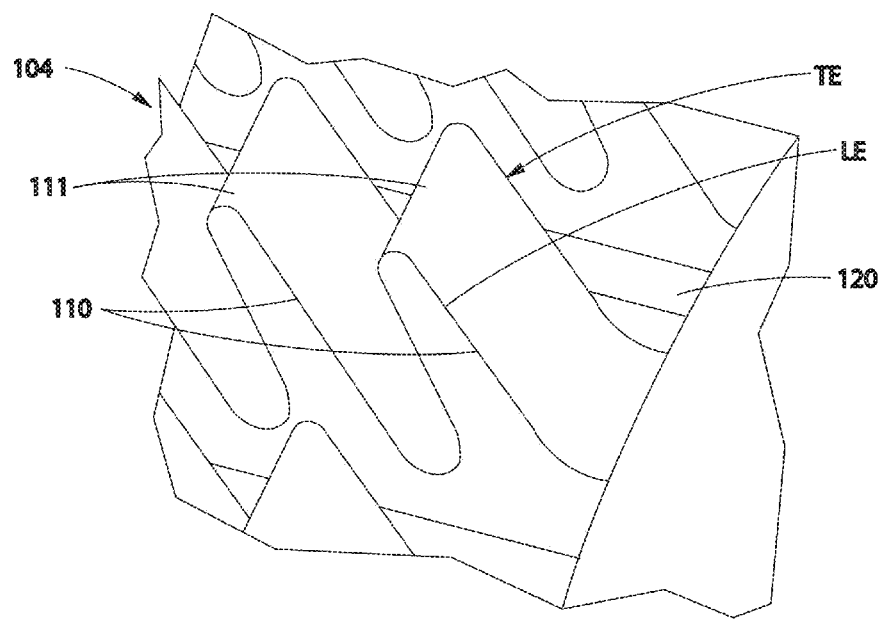
FIG. 10 is an enlarged perspective view of a portion of the apparatus for forming the web of the present invention.

FIG. 9 shows one embodiment of a roll 104 having a plurality of teeth 110 useful for making a terry cloth-like web 1 of spunbond nonwoven material from a spunbond nonwoven precursor web 20 having a basis weight of between about 60 gsm and 100 gsm, preferably about 70 gsm, or 80 gsm or 90 gsm. An enlarged view of teeth 110 shown in FIG. 9 is shown in FIG. 10. In this embodiment of roll 104 teeth 110 have a uniform circumferential length dimension TL of about 1.25 mm measured generally from the leading edge LE to the trailing edge TE at the tooth tip 111, and are uniformly spaced from one another circumferentially by a distance TD of about 1.5 mm. For making a terry-cloth web 1 from a precursor web 20 having a basis weight in the range of about 60 to 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH). Of course, E, P, TH, TD and TL can each be varied independently of each other to achieve a desired size, spacing, and area density of deformations 6 (number of deformations 6 per unit area of web 1).

As shown in FIG. 8, each tooth 110 has a tip 111, a leading edge LE and a trailing edge TE. The tooth tip 111 is elongated and has a generally longitudinal orientation, corresponding to the longitudinal axes L of second regions 4. It is believed that to get the tufted deformations 6 of the web 1 that can be described as being terry cloth-like, the LE and TE should be very nearly orthogonal to the local peripheral surface 120 of roll 104. As well, the transition from the tip 111 and the LE or TE should be a sharp angle, such as a right angle, having a sufficiently small radius of curvature such that, in use the teeth 110 push through precursor web 20 at the LE and TE. Without being bound by theory, it is believed that having relatively sharply angled tip transitions between the tip of tooth 110 and the LE and TE permits the teeth 110 to punch through precursor web 20 "cleanly", that is, locally and distinctly, so that the resulting web 1 can be described as "tufted" in second regions 4 rather than "embossed" for example. When so processed, the web 1 is not imparted with any particular elasticity, beyond what the precursor web 20 may have possessed originally.

It has been found that line speed, that is, the rate at which precursor web 20 is processed through the nip of rotating rolls 102 and 104, and the resulting rate of formation of deformations 6, impacts the structure of the resulting deformations 6. For example, the deformations 6 shown in FIGS. 5 and 6 were made at a relatively low rate of approximately 3 meters per minute (m/min) (about 10 feet per minute). Three m/min is considered a relatively slow rate for commercial production for many consumer applications, but for the spunbond bicomponent fibers used in the nonwoven web shown in FIGS. 5 and 6 this relatively slow speed resulted in very uniform, looped, aligned fibers 8 in deformations 6.

Figure 11:
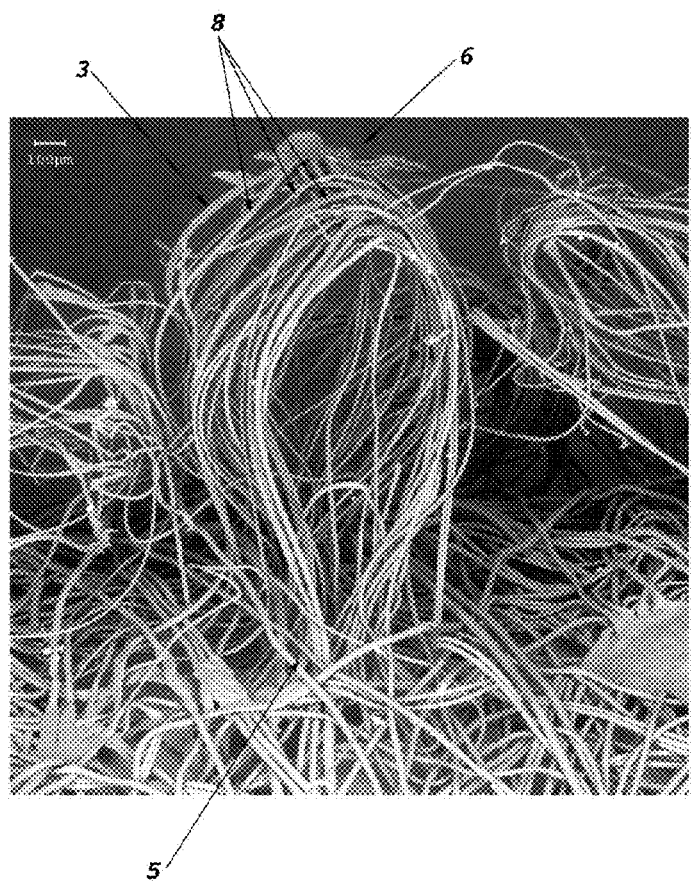
FIG. 11 is a photomicrograph of a portion of a web of the present invention.
Figure 12:
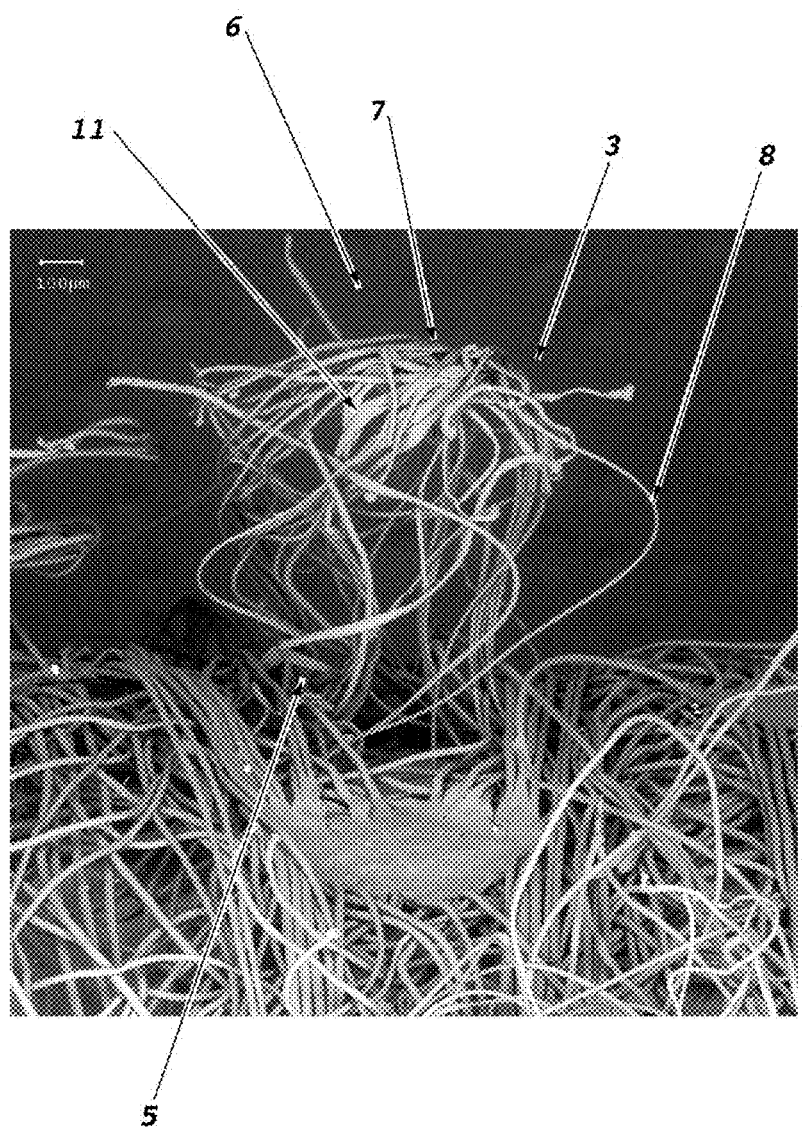
FIG. 12 is a photomicrograph of a portion of a web of the present invention.

At higher line speeds, i.e., relatively higher rates of processing through the nip of rotating rolls 102 and 104, like materials can exhibit very different structures for deformations 6, i.e., tufts. For example, FIGS. 11 and 12 show representative deformations 6 for webs 1 made from the same material with the same process conditions, the only difference being the rotational speed of the rolls 102 and 104, i.e., line speed (in units of length/time) of the precursor web 20 being processed into web 1. The precursor web 20 used for each of the webs shown in FIGS. 11 and 12 was a 25 gsm nonwoven web comprising polypropylene and available from BBA Nonwovens, Simpsonville, S.C., and sold under the trade name Sofspan 200®. The web shown in FIG. 11 was processed through the nip 116 of rolls 102 and 104 having a depth of engagement E of about 3.4 mm (about 0.135 inch), a pitch P of about 1.5 mm (about 0.060 inch), a tooth height TH, of about 3.7 mm (about 0.145 inch), a tooth distance of TD of 1.6 mm (abut 0.063 inch), and a tooth length of TL of about 1.25 mm (about 0.050 inch). The web was run at a line speed of about 15 meters/minute (about 50 feet per minute). The web shown in FIG. 12 is identical to the web shown in FIG. 11, and was processed under identical conditions except for the line speed, which was about 150 meters per minute (about 500 feet per minute).

As can be seen from an inspection of FIGS. 11 and 12, the deformations 6 shown are noticeably different. The deformation 6 shown in FIG. 11 is similar in structure to the deformations shown in FIGS. 1-6. That is, it exhibits substantially aligned, looped fibers 8 with very few broken fibers, e.g., fibers 18 as shown in FIG. 3. The deformation 6 shown in FIG. 12, however, exhibits a very different structure, a structure that appears to be typical of spunbond nonwoven materials processed to form deformations 6 at relatively high speeds. Typical of this structure is broken fibers between the proximal portion, i.e., base 5, of deformations 6 and the distal portion, i.e., the top 3, of deformations 6, and what appears to be a "mat" 7 of fibers at the top of the deformation 6. Mat 7 comprises and is supported at the top of deformations 6 by unbroken, looped fibers 8, and also comprises portions of broken fibers 11 that are no longer integral with precursor web 20. That is, mat 7 comprises fiber portions which were formerly integral with precursor web 20 but which are completely detached from precursor web 20 after processing at sufficiently high line speeds in the process described with reference to FIGS. 7 and 8.

Therefore, from the above description, it is understood that in one embodiment web 1 can be described as being a fibrous web 1 having a first surface 12 and a second surface 14, the fibrous web 1 comprising a first region 2 and a plurality of discrete second regions 4, the second regions 4 having at least one portion being a discontinuity 16 exhibiting a linear orientation and defining a longitudinal axis L and at least another portion being a deformation 6, the deformation 6 comprising fibers integral with but extending from first region 2 and fibers neither integral with nor extending from first region 2.

Figure 13:
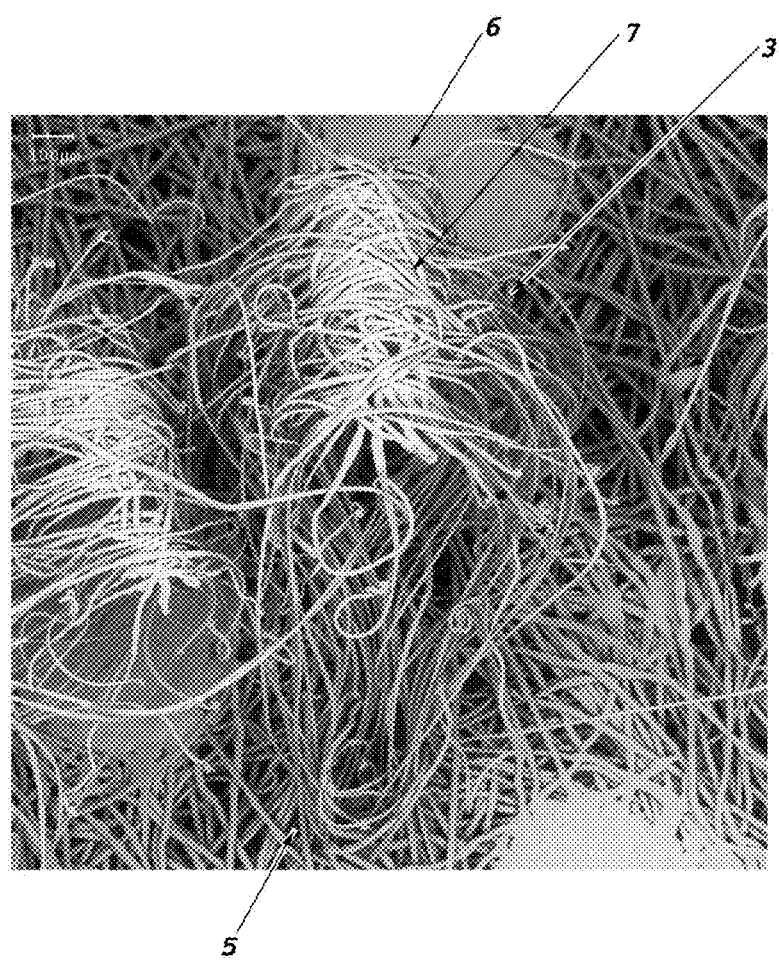
FIG. 13 is a photomicrograph of a portion of a web of the present invention.
Figure 14:
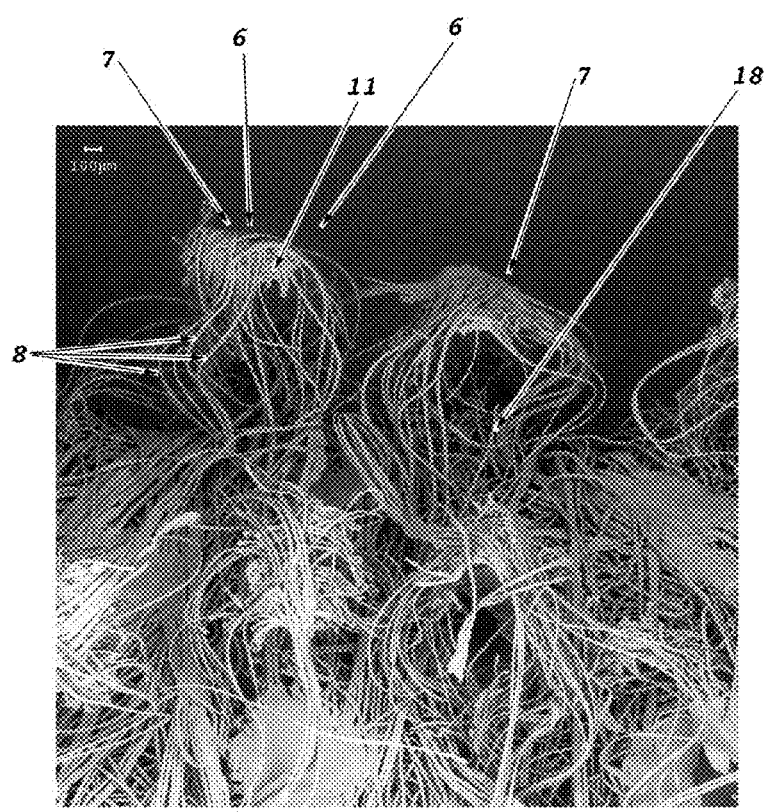
FIG. 14 is a photomicrograph of a portion of a web of the present invention.

Another example of webs 1 being identical in material and processing except for line speed is shown with respect to FIGS. 13 and 14. The precursor web 20 for each web 1 shown in FIGS. 13 and 14 was a 60 gsm spunbond nonwoven web available from BBA Nonwovens, Simpsonville, S.C., and sold under the trade name Sofspan 200®. The web shown in FIG. 13 was processed through the nip 116 of rolls 102 and 104 having a depth of engagement E of about 3.4 mm (about 0.135 inch), a pitch P of about 1.5 mm (about 0.060 inch), a tooth height TH, of about 3.7 mm (about 0.145 inch), a tooth distance of TD of about 1.6 mm (about 0.063 inch), and a tooth length of TL of about 1.25 mm (about 0.050 inch). The web was run at a line speed of about 15 meters/minute (about 50 feet per minute). The web shown in FIG. 14 is identical to the web shown in FIG. 13, and was processed under identical conditions except for the line speed, which was about 150 meters per minute (about 500 feet per minute).

The web 1 shown in FIG. 13 was processed at a line speed of about 15 meters per minute (about 50 feet per minute). As shown, even at this relatively moderate line speed, some amount of matting at the distal end of deformation 6 is noticed. This matting, which appears to be a higher density of flattened, compressed fiber portions, occurs on the portion of deformation 6 associated during manufacturing with the tip of tooth 110 of roll 104. As line speed is increased, this matting, i.e., mat 7, becomes more distinct, as shown in FIG. 14, which shows a web processed under identical conditions as the web shown in FIG. 13, but was processed at a line speed of about 150 meters per minute (about 500 feet per minute). The deformations 6 shown in FIG. 14 exhibit a more distinct mat 7 and can be described as comprising fibers 8 or 18 integral with but extending from first region 2 and fibers 11 (in mat 7) which are neither integral with nor extending from first region 2.

It is believed that the distinct fiber orientation observed at the distal portion of deformations 6, e.g., mat 7, is due primarily to processing rates, it is also believed to be affected by other parameters, such as fiber type and basis weight of the precursor web 20 as well as processing temperatures that can affect the degree of fiber-to-fiber bonding. For example, as observed above, matting of fibers occurs on the portion of deformation 6 associated during manufacturing with the tip of tooth 110 of roll 104. It is believed that frictional engagement of the fibers at the tip of the teeth "lock" the fibers in place, thereby limiting fiber elongation and/or fiber mobility, two mechanisms believed to permit formation of deformations 6. Therefore, once locked, so to speak, in position, fibers adjacent tooth 110 tip can be broken, and, due to the random entanglement of the precursor web as well as possible cold welding of fibers due to pressure and friction, the broken fibers 11 become and remain lodged in mat 7 at the distal end 3 of deformations 6.

Precursor webs 20 having relatively higher basis weights generally have relatively more fiber 11 portions in mat 7. In one sense, it appears as is most of the fiber content of the precursor web 20 in the immediate vicinity of a tooth tip 110 during manufacture is simply displaced in the Z-direction to the distal portion 3 of deformations 6, resulting in mat 7. Precursor webs 20 comprising relatively low elongation fibers, or fibers with relatively low fiber-to-fiber mobility (e.g., relatively limited capability for fiber reptation) appear to result in relatively few fibers becoming and remaining lodged in mat 7 at the distal end 3 of deformations 6. Fiber-to-fiber mobility can be increased by reducing or eliminating the fiber-to-fiber bonds. Thermal bonds can be completely eliminated, or significantly reduced in certain nonwoven webs to increase fiber-to-fiber mobility. Similarly, hydroentangled web can be less entangled to increase fiber-to-fiber mobility. For any precursor web 20 lubricating it prior to processing as disclosed herein can also increase fiber-to-fiber mobility. For example, a mineral oil lubricant can be applied to precursor web 20 prior to it entering the nip 116 of rolls 102 and 104.

The result of the presence of mats 7 is a web 1 having a slightly rougher, textured impression on one side thereof, useful, for example, for wipes in which more scrubbing texture is desirable. In one sense a web having soft terry cloth-like tactile impression when made under relatively low-speed processing conditions, can have the feel of a cheap hotel towel when processed under identical, but relatively higher line speed conditions. This rough, textured tactile impression on a fibrous web can be useful for some applications, such as for a hard surface cleaning wipe or an exfoliating facial wipe.

Figure 17:
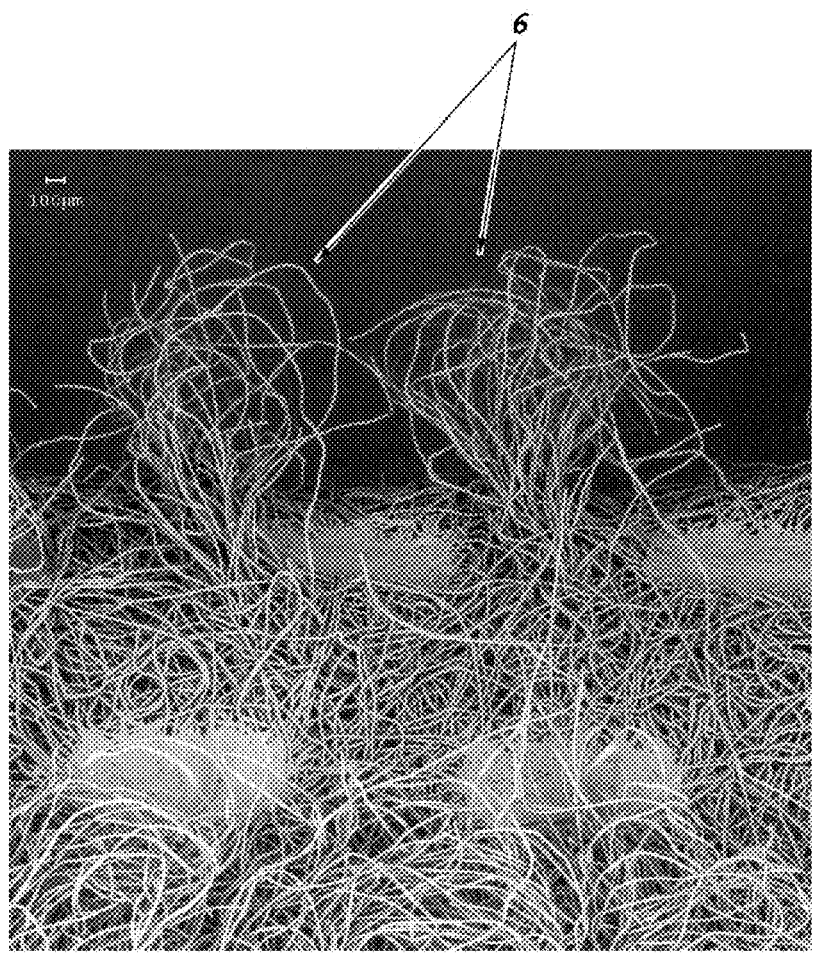
FIG. 17 is a photomicrograph of a portion of a web of the present invention.

It has been found that certain nonwoven webs, such as carded webs comprising staple-length fibers, produce very few looped fibers 8 in deformations 6, so that the deformations 6 produced in these webs cannot be described as comprising a plurality of looped, aligned fibers 8 as described above with respect to FIGS. 1-6. Instead, as shown in the SEM photograph of FIG. 17, carded nonwoven webs can produce deformations 6 having few, if any, looped, aligned fibers 8, and many, if not all, non-aligned fibers and/or broken fibers 18. The precursor web 20 used to make the web 1 shown in FIG. 17 was a 40 gsm carded web available from BBA Nonwovens, Simpsonville, S.C., as High Elongation Carded (HEC®) and was processed through the nip 116 of rolls 102 and 104 having a depth of engagement E of about 3.4 mm (about 0.135 inch), a pitch P of about 1.5 mm (about 0.060 inch), a tooth height TH, of about 3.7 mm (about 0.145 inch), a tooth distance of TD of about 1.6 mm (about 0.063 inch), and a tooth length of TL of about 1.25 mm (about 0.050 inch). The web was run at a line speed of about 15 meters/minute (about 50 feet per minute). It is believed that the non-alignment of fibers in deformations 6 made from carded webs is due in part to the nature of the fiber content of carded webs. Staple fibers are not "endless," but instead have a predetermined length on the order of 25 mm to about 400 mm, and, more typically from about 40 mm to about 80 mm. Therefore, when a carded web is processed by the apparatus described with respect to FIG. 7, it is believed that there is a much greater likelihood that a loose fiber end will be in the vicinity of a deformation 6 and thus produce a non-looped fiber end in deformation 6. Furthermore, often staple fibers do not have the same elongation characteristics of spunbond or melt-blown fibers, for example. However, even if deformations 6 have no looped fibers, the fibrous tufts nevertheless provide a softness benefit and produce a web having terry cloth-like characteristics.

Therefore, from the above description, it is understood that the web of the present invention need not have looped, aligned fibers, and in one embodiment can be described as being a fibrous web 1 formed by selective mechanical deformation of a precursor web 20 having a first surface 12 and a second surface 14 and comprising substantially randomly-oriented fibers, the fibrous web comprising a first region of substantially randomly-oriented fibers being substantially free of deformation by the selective mechanical deformation, and a plurality of discrete integral second regions, the second regions 4 comprising spaced-apart deformations 6 of the precursor web 20, each of the second regions 4 having at least one portion being a discontinuity 16 exhibiting a linearity and defining a longitudinal axis L and at least another portion comprising a plurality of tufted fibers integral with but extending from said first region.

Webs 1 of the present invention offer many opportunities for producing engineered materials having selected characteristics. For example, a web 1 can be made by selecting the length of staple fibers in a carded precursor web 20 so that the probability of having fiber ends exposed in deformations 6 can be reliably predicted. Also, a carded web of staple fibers can be blended or laminated with a spunbond nonwoven web to produce a hybrid, such that the deformations 6 of second regions 4 comprise primarily looped spunbond fibers and the first regions 2 comprise both carded and spunbond fibers. The type of fibers, the length of staple fibers, the layering of fibers, and other variations of precursor web 20 can be varied as desired to produce desired functional characteristics of the web 1.

If a woven precursor web 20 is utilized, the formation and structure of second regions 4 can be very close to the same as that exhibited by webs 1 formed from nonwoven webs. For example, if a woven precursor web 20 has warp or weft threads having sufficient elongation properties and being predominantly oriented in a cross machine direction, upon being processed by the apparatus 100 described above, the teeth 110 tend to separate the machine direction threads (either warp or weft) and only urge out of plane the cross-machine direction threads. Thus, the web 1 produced from a woven precursor web 20 can look and feel very much like terry cloth fabric.

In preferred embodiments precursor web 20 is a nonwoven web in which there are minimal fiber-to-fiber bonds. For example, the precursor web can be a nonwoven web having a pattern of discrete thermal point bonds, as is commonly known in the art for nonwoven webs. In general, however, it is desirable to minimize the number and spacing of bond points so as to allow for maximum fiber mobility and dislocation at the second regions 4 of web 1. In general, utilizing fibers having relatively high diameters, and/or relatively high extension to break, and/or relatively high fiber mobility, results in better and more distinctly formed second regions 4, specifically deformations 6.

Although web 1 is disclosed in preferred embodiments as a single layer web made from a single layer precursor web 20, it is not necessary that it be so. For example, a laminate or composite precursor web 20 having two or more layers or plies can be used. In general, the above description for web 1 holds, recognizing that looped aligned fibers 8, for example, formed from a laminate precursor web would be comprised of fibers from both (or all) layers of the laminate. In such a web structure, it is important, therefore, that all the fibers of all the layers have sufficient diameter, elongation characteristics, and fiber mobility, so as not to break prior to extension and deformation. In this manner, fibers from all the layers of the laminate may contribute to the tufted deformations 6. In a multilayer web, the fibers of the different webs may be mixed or intermingled in the deformation 6. The fibers do not protrude through but combine with the fibers in an adjacent web. This is often observed when the webs are processed at very high speeds.

Figure 18:
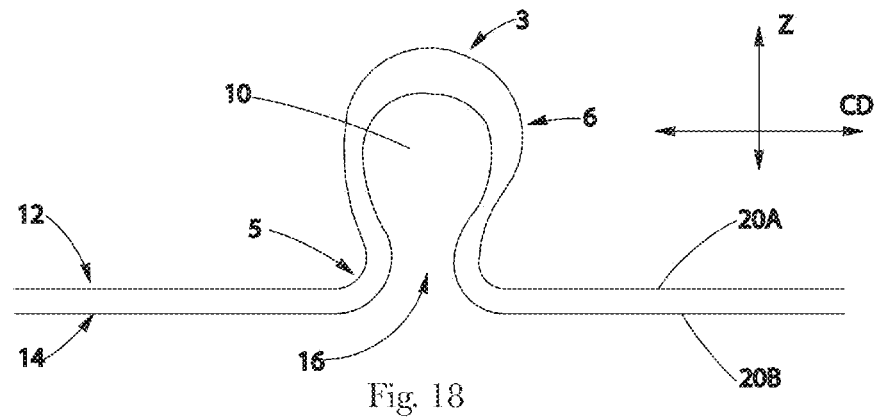
FIG. 18 is a schematic representation of a portion of a web of the present invention.
Figure 19:
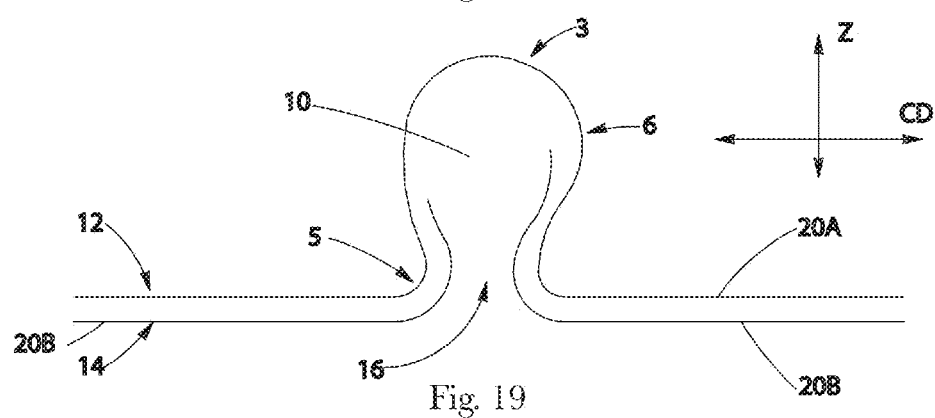
FIG. 19 is another schematic representation of a portion of a web of the present invention.
Figure 20:
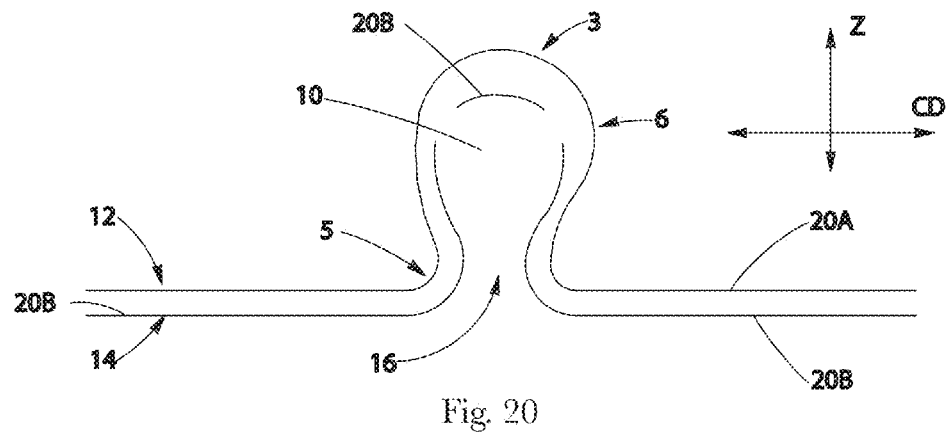
FIG. 20 is another schematic representation of a portion of a web of the present invention.

Multilayer webs 1 can have significant advantages over single layer webs 1. For example, a deformation 6 from a multilayer web 1 using two precursor webs 20A and 20B is shown schematically in FIGS. 18-20. As shown, both precursor webs 20A and 20B contribute fibers to deformations 6 in a "nested" relationship that "locks" the two precursor webs together, forming a laminate web without the use or need of adhesives or thermal bonding between the layers. However, if desired an adhesive, chemical bonding, resin or powder bonding, or thermal bonding between the layers can be selectively utilized to certain regions or all of the precursor webs. In addition, the multiple layers may be bonded during processing, for example, by extruding a film onto a nonwoven or carding one layer of nonwoven onto a spundbond and thermal point bonding the combined layers. In a preferred embodiment, the deformations 6 retain the layered relationship of the laminate precursor web, as shown in FIG. 18, and in all preferred embodiments the upper layer (specifically layer 20A in FIGS. 18-20, but in general the top layer with reference to the Z-direction as shown in FIGS. 18-20) remains substantially intact and forms looped fibers 8.

Figure 15:
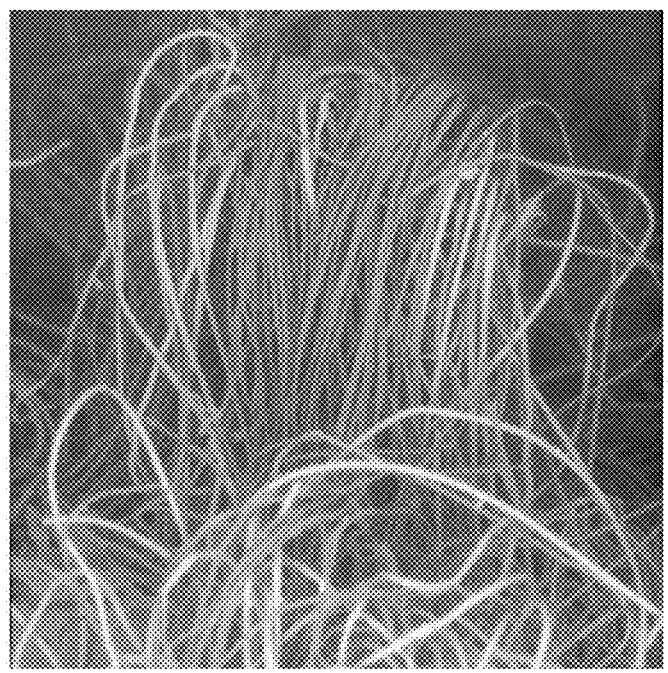
FIG. 15 is a photomicrograph of a portion of a web of the present invention.
Figure 16:
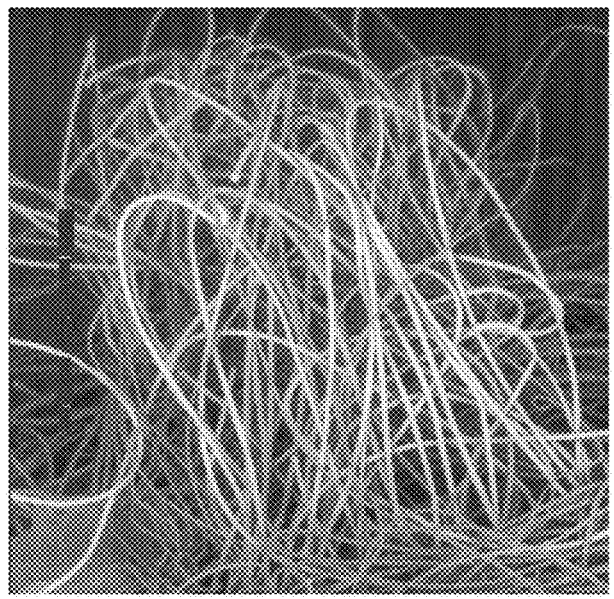
FIG. 16 is a photomicrograph of a portion of a web of the present invention.

In a multilayer web 1 each precursor web can have different properties. For example, web 1 can comprise two (or more) precursor webs, e.g., first and second precursor webs 20A and 20B. First precursor web 20A can form an upper layer exhibiting high elongation and significant elastic recovery which enables the web 20A to spring back. The spring back helps to laterally squeeze the base portion 5 of the deformation 6 of both webs as shown in FIG. 18. The spring back or lateral squeeze also helps to secure and stabilize the Z-oriented fibers in the deformation 6. The lateral squeeze provided by precursor web 20A can also increase the stability of the second precursor web 20B. An example of a multilayer web 1 being identical in material and processing except for the line speed is shown with respect to FIGS. 15 and 16. Multilayer web 1 as shown in FIGS. 15 and 16 includes a first precursor web 20A comprised of spunbond PE/PP sheath/core nonwoven web made by BBA, Washougal Wash. The second precursor web 20B is comprised of a thermal point bonded carded PET/Co-PET nonwoven web (50% 6 dpf PET Wellman Type 204 made in Charlotte N.C. and 50% 6 dpf Co-PET Kanematsu Type LM651 made in Gastonia N.C. The second precursor web 20B can be loosely bonded to enable tufting so the lateral squeeze of the first precursor web 20A can also increase the stability of the second precursor web 20B. The multilayer webs 1 were both processed at a depth of engagement E of about 3.4 mm (about 0.135 inch). The multilayer web 1 shown in FIG. 15 was processed at a slow speed, 3 meters per minute, and the multilayer web 1 shown in FIG. 16 was processed at a high speed, of 150 meters per minute. As can be seen, the fibers from the first and second precursor webs 20A and 20B in the deformation 6 in FIG. 16 (high speed processing) are much more intermingled than those shown in FIG. 15 (slow speed processing). The multilayer web 1 can be utilized as a body-contacting layer when used as a topsheet on a disposable absorbent article.

In a multilayer web 1 each precursor web can have different material properties, thereby providing web 1 with beneficial properties. For example, web 1 comprising two (or more) precursor webs, e.g., first and second precursor webs 20A and 20B can have beneficial fluid handling properties for use as a topsheet on a disposable absorbent article, as described more fully below. For superior fluid handling, for example, first precursor web 20A can form an upper layer (i.e., a body-contacting when used as a topsheet on a disposable absorbent article) and be comprised of relatively hydrophobic fibers. Second precursor web 20B can form a lower layer (i.e., disposed between the topsheet and an absorbent core when used on a disposable absorbent article) comprised of relatively hydrophilic fibers. Fluid deposited upon the upper, relatively hydrophobic layer is quickly transported to the lower, relatively hydrophilic, layer. One reason for the observed rapid fluid transport is the capillary structures formed by the generally aligned fibers 8, 18 of deformations 6. The fibers 8, 18 form directionally-aligned capillaries between adjacent fibers, and the capillary action is enhanced by the general convergence of fibers near proximal portion 5 of deformations 6.

It is believed that the rapid fluid transport is further increased due to the ability of fluid to enter the web 1 via the voids 10 created by deformations 6. This "lateral entry" capability and/or capillary action, and/or the hydrophilicity gradient afforded by the structure of web 1 makes web 1 an ideal material for optimal fluid handling for disposable absorbent articles. In particular, a multilayer web 1 can provide for even greater improvement in fluid handling characteristics. In another embodiment, first precursor web 20A can be comprised of relatively soft fibers (e.g., polyethylene), while second precursor web 20B can be comprised of relatively stiff fibers (e.g., polyester). In such a multilayer web 1, deformations 6 can retain or recover a certain amount of height h, even after applied pressure. The benefit of such as structure, particularly when combined with a hydrophilicity gradient as described above (fibers can be rendered hydrophobic or hydrophilic by means known in the art), is a web 1 suitable for use as a topsheet in feminine hygiene products that provides for superior fluid acquisition and superior rewet properties (i.e., reduced fluid movement back to the surface of the topsheet). It is believed that the increased stiffness provided by the relatively stiff fibers of second precursor web 20B provide for increased compression resistant caliper (thickness) of the web, while the relatively soft fibers of first precursor web 20A provides for softness at the web/skin interface. This extra caliper, together with the ability of the distally-disposed portions 3 of deformations 6 to remain relatively soft and relatively fluid free, results in a superior, soft, dry (and dry-feeling) topsheet for use in feminine hygiene products, as well as baby diapers, adult incontinence articles, bandages, and the like.

FIGS. 18-20 show representative schematic diagrams of possible structures for deformation 6, depending on the material properties of precursor webs 20A or 20B. Other structures, not shown, can be achieved, with the only limitation to various structures being the limitations inherent in the material properties of the precursor webs.

Therefore, as can be seen from the above description, depending on the precursor web 20 (or webs) utilized and the dimensional parameters of rolls 102 and 104, including teeth 110, web 1 of the present invention can exhibit a wide range of physical properties. The web 1 can exhibit a range of texture subjectively experienced as ranging from softness to roughness, an absorbency ranging from non-absorbent to very absorbent, a bulkiness ranging from relatively low bulk to relatively high bulk; a tear strength ranging from low tear strength to high tear strength; an elasticity ranging from non-elastic to at least 100% elastically extensible, a chemical resistance ranging from relatively low resistance to high resistance, depending on the chemical considered, and many other variable parameters generally described as shielding performance, alkali resistance, opacity, wiping performance, water absorptivity, oil absorptivity, moisture permeability, heat insulating properties, weatherability, high strength, high tear force, abrasion resistance, electrostatic controllability, drape, dye-affinity, safety and the like. In general, depending on the elongation properties of the fibers of precursor web 20, the dimensions of apparatus 100 can be varied to produce a web 1 having a wide range of dimensions associated with second regions 4, including the height h (as shown in FIG. 22), and spacing, including the area density of discrete second regions 4).

Web 1 may be used for a wide variety of applications, including various filter sheets such as air filter, bag filter, liquid filter, vacuum filter, water drain filter, and bacterial shielding filter; sheets for various electric appliances such as capacitor separator paper, and floppy disk packaging material; various industrial sheets such as tacky adhesive tape base cloth, oil absorbing material, and paper felt; various wiper sheets such as wipers for homes, services and medical treatment, printing roll wiper, wiper for cleaning copying machine, and wiper for optical systems; hygiene or personal cleansing wiper such as baby wipes, feminine wipes, facial wipes, or body wipes, various medicinal and sanitary sheets, such as surgical gown, gown, covering cloth, cap, mask, sheet, towel, gauze, base cloth for cataplasm, diaper, diaper core, diaper acquisition layer, diaper liner, diaper cover, base cloth for adhesive plaster, wet towel, and tissue; various sheets for clothes, such as padding cloth, pad, jumper liner, and disposable underwear; various life material sheets such as base cloth for artificial leather and synthetic leather, table top, wall paper, shoji-gami (paper for paper screen), blind, calendar, wrapping, and packages for drying agents, shopping bag, suit cover, and pillow cover; various agricultural sheets, such as cow carpets, cooling and sun light-shielding cloth, lining curtain, sheet for overall covering, light-shielding sheet and grass preventing sheet, wrapping materials of pesticides, underlining paper of pots for seeding growth; various protection sheets such as fume prevention mask and dust prevention mask, laboratory gown, and dust preventive clothes; various sheets for civil engineering building, such as house wrap, drain material, filtering medium, separation material, overlay, roofing, tuft and carpet base cloth, wall interior material, soundproof or vibration reducing sheet, and curing sheet; and various automobile interior sheets, such as floor mat and trunk mat, molded ceiling material, head rest, and lining cloth, in addition to a separator sheet in alkaline batteries.

Figure 21:
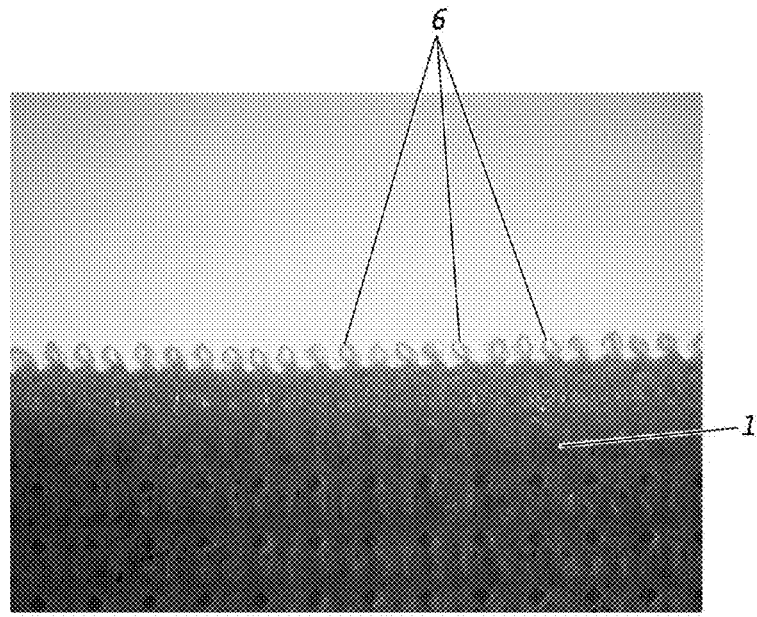
FIG. 21 is a photomicrograph of a portion of a web of the present invention.

FIG. 21 is a photomicrograph of a terry cloth-like nonwoven fabric web 1 made by the process of the present invention using a roll 104 as shown in FIGS. 9 and 10 and useful as a component of a disposable absorbent article (as shown below in FIG. 23). The precursor web 20 used for the web 1 shown in FIG. 21 was a spunbond nonwoven having a basis weight of about 80 gsm, and comprising polyethylene/polypropylene (sheath/core) polyethylene/polypropylene (sheath/core) bicomponent fibers having an average diameter of about 33 microns. The web 1 of FIG. 21 has about 24 deformations 6 per square centimeter and is folded with the folded edge visible to show more clearly a plurality of spaced apart, tufted, looped deformations 6 having a plurality of looped, aligned fibers 8, each of which has an average fiber diameter of about 18 microns.

Figure 22:
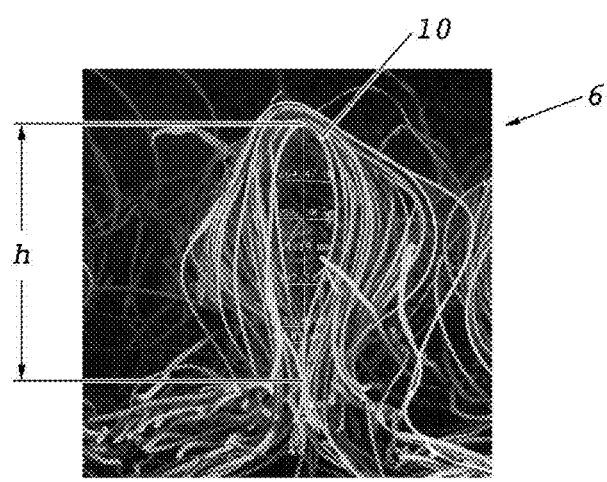
FIG. 22 is an enlarged photograph of a portion of the web shown in FIG. 18.

A single deformation 6 is shown in FIG. 22 with dimensions indicated. As shown in FIG. 10, for the web described with respect to FIG. 22, the void area 10 of tufted, looped, deformation 6 is typically generally circular or oblong in shape, having a major dimension, referred to as height h, that can be at least 1 mm. In general, the height is not considered to be critical to the operation of the web, but can be varied depending on the desired end use of web 1. The height h can be from 0.1 mm to about 10 mm or more. A web 1 formed from a nonwoven precursor web 20 and having a look and feel of terry cloth should have a height h of about 1 mm to about 3 mm.

Table 1 below shows representative dimensions for representative apparatus and webs made thereon.

TABLE 1

Examples of Apparatus Dimensional Parameters and Web Dimensions

| Sample No. | Precursor Web | Pitch (P) <mm> (inches) | Engagement (E) <mm> (inches) | Tooth Height (TH) <mm> (inches) | Loop height (h) (mm) | Avg. Fiber Diameter of Precursor Web (μm) | Avg. Fiber Diameter of Loop Fiber (μm) |
|---|---|---|---|---|---|---|---|
| 1 | 80 gsm spunbond PE/PP core/sheath | <1.5> (0.060) | <3.4> (0.135) | <3.7> (0.145) | 1.07 | 33 | 18 |
| 2 | 80 gsm spunbond PE/PP core/sheath | <1.5> (0.060) | <2.2> (0.085) | <3.7> (0.145) | 0.49 | 31 | 23 |
| 3 | 60 gsm spunbond PE/PP copolymer | <1.5> (0.060) | <3.4> (0.135) | <3.7> (0.145) | 1.10 | 23 | 14 |

TABLE 1-continued

Examples of Apparatus Dimensional Parameters and Web Dimensions

| Sample No. | Precursor Web | Pitch (P) <mm> (inches) | Engagement (E) <mm> (inches) | Tooth Height (TH) <mm> (inches) | Loop height (h) (mm) | Avg. Fiber Diameter of Precursor Web (μm) | Avg. Fiber Diameter of Loop Fiber (μm) |
|---|---|---|---|---|---|---|---|
| 4 | 60 gsm spunbond PE/PP copolymer | <1.5> (0.060) | <3.4> (0.135) | <3.7> (0.145) | 1.41 | 28 | 15 |

In Table 1 above, all Samples are available from BBA Nonwovens, Simpsonville, S.C. Samples 1 and 2 are sold under the trade name Softex®. Samples 3 and 4 are sold under the trade name Sofspan 200®.

Figure 23:
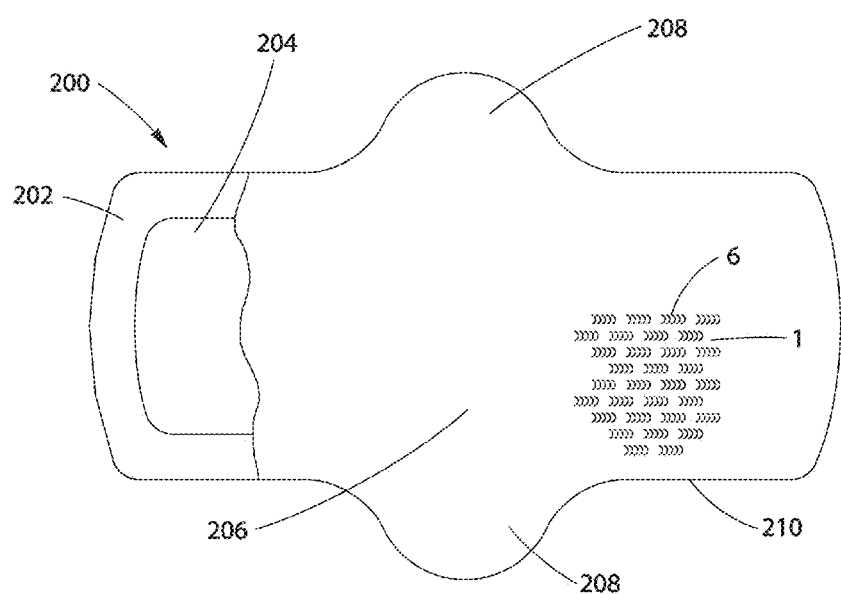
FIG. 23 is a partial cut away plan view of a sanitary napkin of the present invention.

FIG. 23 shows in partial cut away plan view a catamenial article, specifically a sanitary napkin, having as one of its components a web 1 of the present invention. In general, sanitary napkin 200 comprises a backsheet 202, a topsheet 206 and an absorbent core 204 disposed between the topsheet 206 and backsheet 202 which can be joined about a the periphery 210. Sanitary napkin 200 can have side extensions, commonly referred to as "wings" 208 designed to wrap the sides of the crotch region of the panties of the user of sanitary napkin 1. Topsheet 206 of sanitary napkin 200 comprises web 1 having deformations 6 on a body facing side thereof. Alternatively, web 1 could be used with the deformation 6 on side 12 opposite of the body-facing side and the second side 14 being the body-facing side. This may enable the discontinuities 16 to transport fluid into the deformations 6. Sanitary napkins, including topsheets for use as the body facing surface thereof, are well known in the art and need no detailed description of various alternative and optional designs. Other catamenial articles, such as panty liners, interlabial devices, will also have similar structure as sanitary napkins. It is noted that web 1 can be used as, or as a component of, one or more of a backsheet, core material, topsheet, secondary topsheet, or wing material. For example, web 1 could have multiple layers and comprise the topsheet, secondary topsheet, core and/or backsheet of hygiene product.

Web 1 can be utilized as an absorbent core in a hygiene product. The web 1 in an absorbent core may have a relatively high basis weight and/or be comprised of several layers. Specifically, an absorbent core can comprise a fibrous web of randomly oriented fibers with respect to an X-Y plane. The core will comprise a first surface and a second surface. The first surface will comprise a plurality of discrete regions of fiber reorientation. Each discrete region will have a linear orientation defining a longitudinal axis in the X-Y plane and will comprise a plurality of fibers having portions reoriented in a direction substantially orthogonal to said X-Y plane.

Web 1 or a composite comprising web 1 can also be utilized as a fecal material storage element. Web 1 can be utilized as a secondary topsheet or sublayer when it is disposed under an apertured web or film to accept and hold low viscosity feces or viscous bodily waste away from a wearer's skin after defecation. Embodiments of the present invention having larger total three dimensional volume within the web or between the deformations 6 generally provide a greater capacity for storage of low viscosity feces. Absorbent articles employing such fecal material storage elements, or sublayers, are described in U.S. Pat. Nos. 5,941,864; 5,957,906; 6,018,093; 6,010,491; 6,186,992; and 6,414,215, among others.

Figure 24:
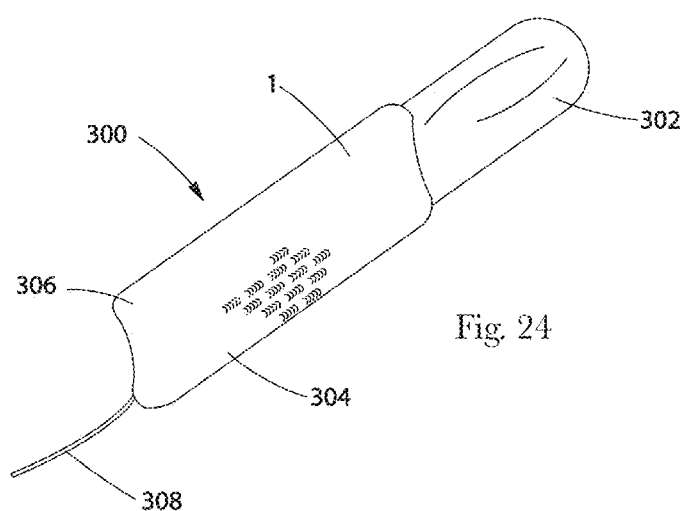
FIG. 24 is a partial cut away perspective view of a tampon of the present invention.

FIG. 24 shows in partial cut away perspective view a catamenial tampon 300 having as one of its components a web 1 of the present invention. In general, tampon 300 comprises a compressed absorbent core 302 and a fluid permeable cover wrap 304 that covers absorbent core 302. Cover wrap 304 may extend beyond one end of absorbent core 302 to form a skirt portion 306. A removal means, such as string 308 can be provided to facilitate removal of the tampon after use. Tampons, including cover wraps for use as the body contacting surface thereof, are well known in the art and need no detailed description of various alternative and optional designs. However, it is noted that web 1 can be used as, or as a component of, one or more of a cover wrap, absorbent core material, or removal means material.

Another advantage of the process described to produce the webs of the present invention is that the webs can be produced in-line with other web production equipment or in-line with disposable absorbent article production equipment. Additionally, there may be other solid state formation processes that can be used either prior to or after the process of the present invention. For example, portions of or all of a web could be processed according to the present invention and then apertured with a stretching process, such as one described in U.S. Pat. No. 5,658,639 to Curro et al. Alternatively, a material could be made into a composite through a variety of processes, such as one described in US Publication No. 2003/028,165A1 to Curro et al. or ring rolled, for example as in U.S. Pat. No. 5,167,897 to Weber et al. and then processed according to the present invention. The resulting webs can thus exhibit the combined benefits of these multiple material modifications.

As can be understood from the above description of webs 1 and apparatus 100 of the present invention, many various structures of webs 1 can be made without departing from the scope of the present invention as claimed in the appended claims. For example, webs 1 can be coated or treated with lotions, medicaments, cleaning fluids, anti-bacterial solutions, emulsions, fragrances, surfactants. Likewise, apparatus 100 can be configured to only form deformations 6 on a portion of the web 1, or to form varying sizes or area densities of deformations 6.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multilayer web comprising:
   a. a first nonwoven;
   b. a second nonwoven that is different from the first nonwoven; and
   c. a plurality of fiber tufts extending from a surface of one of the first nonwoven and the second nonwoven, the plurality of fibers tufts comprising fibers from both the first nonwoven and the second nonwoven;
   d. wherein the difference between the first nonwoven and the second nonwoven is their fiber composition; and
   e. wherein at least some of the plurality of fiber tufts comprise fibers that are integral with and extend from one of the first nonwoven and the second nonwoven, and that extend completely through the other of the first nonwoven and the second nonwoven.

2. The multilayer web of claim 1, wherein the first nonwoven comprises relatively hydrophobic fibers and the second nonwoven comprises relatively hydrophilic fibers.

3. The multilayer web of claim 1, wherein the first nonwoven comprises substantially continuous fibers and the second nonwoven comprises staple fibers.

4. The multilayer web of claim 1, wherein the first nonwoven comprises polyethylene fibers and the second nonwoven comprises polyester fibers.

5. The multilayer web of claim 1, wherein at least one of the first nonwoven and the second nonwoven comprises cellulose, rayon, and/or cotton fibers.

6. The multilayer web of claim 1, wherein at least one of the first nonwoven and the second nonwoven comprises splittable fibers.

7. The multilayer web of claim 1, wherein at least one of the first nonwoven and the second nonwoven comprises nanofibers.

8. The multilayer web of claim 1, wherein at least one of the first nonwoven and the second nonwoven comprises non-round fibers.

9. The multilayer web of claim 1, wherein the first nonwoven comprises bicomponent fibers and the second nonwoven comprises monocomponent fibers.

10. A personal hygiene product comprising the multilayer web of claim 1, wherein the personal hygiene product has a body facing side and wherein the plurality of fiber tufts extend in a direction opposite to the body facing side.

11. The personal hygiene product of claim 10, wherein the multilayer web at least partially forms a topsheet or secondary topsheet of the personal hygiene product.

12. A personal hygiene product comprising the multilayer web of claim 1, wherein the first nonwoven forms a body facing side of the personal hygiene product.

13. A personal hygiene product comprising the multilayer web of claim 1, wherein the second nonwoven forms a body facing side of the personal hygiene product.

14. A multilayer web comprising:
   a. a first nonwoven;
   b. a second nonwoven that is different from the first nonwoven; and
   c. a plurality of fiber tufts extending from a surface of one of the first nonwoven and the second nonwoven, the plurality of fibers tufts comprising fibers from both the first nonwoven and the second nonwoven;
   d. wherein the difference between the first nonwoven and the second nonwoven is their construction; and
   e. wherein at least some of the plurality of fiber tufts comprise fibers that are integral with and extend from one of the first nonwoven and the second nonwoven, and that extend completely through the other of the first nonwoven and the second nonwoven.

15. The multilayer web of claim 14, wherein the first nonwoven is a spunbond nonwoven and the second nonwoven is a thermal bonded, carded nonwoven.

16. The multilayer web of claim 14, wherein the spunbond nonwoven comprises side-by-side configured bicomponent fibers.

17. The multilayer web of claim 14, wherein the first nonwoven is a hydroentangled nonwoven.

18. The multilayer web of claim 14, wherein the plurality of fiber tufts comprises looped fibers.

19. A personal hygiene product comprising the multilayer web of claim 14, wherein the personal hygiene product has a body facing side and wherein the plurality of fiber tufts extend in a direction opposite to the body facing side.

20. The personal hygiene product of claim 19, wherein the multilayer web at least partially forms a topsheet or secondary topsheet of the personal hygiene product.

21. A personal hygiene product comprising the multilayer web of claim 14, wherein the first nonwoven forms a body facing side of the personal hygiene product.

22. A personal hygiene product comprising the multilayer web of claim 14, wherein the second nonwoven forms a body facing side of the personal hygiene product.

* * * * *